(12) United States Patent
Noh et al.

(10) Patent No.: US 12,156,465 B2
(45) Date of Patent: Nov. 26, 2024

(54) SPACE-THROUGH CHARGE TRANSFER COMPOUND, AND ORGANIC LIGHT EMITTING DIODE AND ORGANIC LIGHT EMITTING DISPLAY DEVICE INCLUDING THE SAME

(71) Applicant: LG Display Co., Ltd, Seoul (KR)

(72) Inventors: Hyo-Jin Noh, Paju-si (KR); Kyung-Jin Yoon, Paju-si (KR); Bo-Min Seo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 495 days.

(21) Appl. No.: 16/428,758

(22) Filed: May 31, 2019

(65) Prior Publication Data
US 2019/0372013 A1    Dec. 5, 2019

(30) Foreign Application Priority Data
Jun. 1, 2018    (KR) .................. 10-2018-0063614

(51) Int. Cl.
*H10K 85/60*    (2023.01)
*C07D 403/10*    (2006.01)
(Continued)

(52) U.S. Cl.
CPC ......... *H10K 85/654* (2023.02); *C07D 403/10* (2013.01); *C09K 11/02* (2013.01);
(Continued)

(58) Field of Classification Search
CPC ............. H01L 51/0067; H01L 51/0072; H01L 51/5092; H01L 51/5016; H01L 51/5004;
(Continued)

(56) References Cited

U.S. PATENT DOCUMENTS 10,270,042 B2    4/2019  Lee et al.
2010/0084647 A1*  4/2010  Kondakova ......... H01L 51/0067
                                                257/E51.026
(Continued)

FOREIGN PATENT DOCUMENTS

CN    106316924 A  *  1/2017  ........... C07D 209/82
CN    107445962 A    12/2017
(Continued)

OTHER PUBLICATIONS

Shaolong Gong "Simple CBP isomers with high triplet energies for highly efficient blue electrophosphorescence" J. Mater. Chem., 2012, 22, 2894 (Year: 2012).*
(Continued)

*Primary Examiner* — Michael Y Sun
(74) *Attorney, Agent, or Firm* — Seed IP Law Group LLP

(57) ABSTRACT

The present disclosure provides a space-through charge transfer compound of following formula and an organic light emitting diode and an organic light emitting display device including the space-through charge transfer compound.

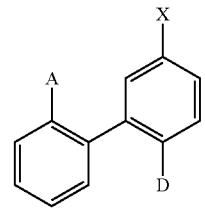

21 Claims, 7 Drawing Sheets

(51) Int. Cl.
| | |
|---|---|
| *C09K 11/02* | (2006.01) |
| *C09K 11/06* | (2006.01) |
| *H10K 50/11* | (2023.01) |
| *H10K 50/15* | (2023.01) |
| *H10K 50/16* | (2023.01) |
| *H10K 50/17* | (2023.01) |
| *H10K 50/18* | (2023.01) |
| *H10K 101/10* | (2023.01) |
| *H10K 101/30* | (2023.01) |
| *H10K 101/40* | (2023.01) |

(52) U.S. Cl.
CPC .......... *C09K 11/06* (2013.01); *H10K 85/6572* (2023.02); *C09K 2211/1007* (2013.01); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02); *H10K 2101/30* (2023.02); *H10K 2101/40* (2023.02)

(58) Field of Classification Search
CPC .......... H01L 2251/552; H01L 51/5096; H01L 51/5056; H01L 51/5072; H01L 51/5088; H01L 51/0071; H01L 51/5012; C09K 11/02; C09K 11/06; C09K 2211/1018; C09K 2211/1007; C09K 2211/1029; C09K 2211/1044; C09K 2211/1088; C09K 2211/1059; C07D 403/10; C07D 491/107; C07D 403/14; C07D 401/10
See application file for complete search history.

(56) References Cited

U.S. PATENT DOCUMENTS

2016/0111659 A1* 4/2016 Yang .................. H10K 85/6572
546/276.7
2016/0181562 A1* 6/2016 Pieh .................... H01L 51/5218
257/40

FOREIGN PATENT DOCUMENTS

| | | | | |
|---|---|---|---|---|
| DE | 102016121562 A1 | * | 5/2018 | .......... C07D 403/10 |
| JP | 2013123056 A | * | 6/2013 | |
| KR | 10-2018-0028179 A | | 3/2018 | |
| WO | WO-2016052819 A1 | * | 4/2016 | .......... C07D 209/82 |

OTHER PUBLICATIONS

Ming-Shiang Lin "Incorporation of a CN group into mCP: a new bipolar host material for highly efficient blue and white electrophosphorescent devices" J. Mater. Chem., 2012, 22, 16114 (Year: 2012).*
Roberta Ragni "Organic and Organometallic Fluorinated Materials for Electronics and Optoelectronics: A Survey on Recent Research" Eur. J. Org. Chem. 2018, 3500-3519 (Year: 2018).*
Chunmiao Han "A Simple Phosphine-Oxide Host with a Multi-insulating Structure: High Triplet Energy Level for Efficient Blue Electrophosphorescence" Chem. Eur. J. 2011, 17, 5800-5803 (Year: 2011).*
Jiyoung Lee "Versatile Molecular Functionalization for Inhibiting Concentration Quenching of Thermally Activated Delayed Fluorescence" Adv. Mater. 2017, 29, 1604856 (Year: 2017).*
Zhang et al., "Efficient blue organic light-emitting diodes employing thermally activated delayed Fluorescence," *Nature Photonics* 8:326-332, 2014.

* cited by examiner

SPACE-THROUGH CHARGE TRANSFER COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

This application claims priority to and the benefit of Republic of Korea Patent Application No. 10-2018-0063614 filed on Jun. 1, 2018, which is hereby incorporated by reference in its entirety.

BACKGROUND

Technical Field

The present disclosure relates to an emitting material and more particularly to a space-through charge transfer compound having excellent emitting efficiency and an organic light emitting diode (OLED) and an organic light emitting display device including the space-through charge transfer compound.

Description of the Related Art

The requirements of the large-size display device have led to developments in flat panel display devices as an image displaying device. Among the flat panel display devices, the OLED has rapidly developed.

In the OLED, when the electron from a cathode, which serves as an electron-injecting electrode, and the hole from an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption, and color purity.

The OLED includes a first electrode as an anode on a substrate, a second electrode as a cathode facing the first electrode, and an organic emitting layer therebetween.

To improve the emitting efficiency, the organic emitting layer may include a hole injection layer (HIL), a hole transporting layer (HTL), an emitting material layer (EML), an electron transporting layer (HTL), and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such the light is emitted.

The External quantum efficiency of the emitting material for the EML can be expressed by the following equation:

$$\eta_{ext} = \eta_{int} \times \Gamma \times \Phi \times \eta_{out\text{-}coupling}$$

In the above equation, "$\eta_{int}$" is the internal quantum efficiency, "$\Gamma$" is the charge balance factor, "$\Phi$" is the radiative quantum efficiency, and "$\eta_{out\text{-}coupling}$" is the out-coupling efficiency.

The charge balance factor "r" means a balance between the hole and the electron when generating the exciton. Generally, assuming 1:1 matching of the hole and the electron, the charge balance factor has a value of "1". The radiative quantum efficiency "$\Phi$" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of holes and electrons. In the fluorescent compound, a maximum value of the internal quantum efficiency is 0.25. When the hole and the electron are combined to generate the exciton, a ratio of the singlet excitons to the triplet excitons is 1:3 according to the spin structure. However, in the fluorescent compound, only the singlet excitons excluding the triplet excitons are engaged in emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed as 0.2.

Accordingly, the maximum emitting efficiency of the OLED including the fluorescent compound as the emitting material is less than approximately 5%.

To overcome the disadvantage of the emitting efficiency of the fluorescent compound, the phosphorescent compound, where both the singlet excitons and the triplet excitons are engaged in the emission, has been developed for the OLED.

The red and green phosphorescent compounds having a relatively high efficiency are introduced and developed. However, there is no blue phosphorescent compound meeting the requirements in emitting efficiency and reliability.

BRIEF SUMMARY

Accordingly, the embodiment of the present disclosure is directed to a space-through charge transfer compound and an OLED and an organic light emitting display device using the same that substantially obviate one or more of the problems due to limitations and disadvantages of the related art.

An objective of the embodiment of the present disclosure is to provide a space-through charge transfer compound having high emitting efficiency.

Another objective of the embodiment of the present disclosure is to provide an OLED and an organic light emitting display device having improved emission efficiency.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

To achieve these and other advantages and in accordance with the purpose of the embodiments of the disclosure, as embodied and broadly described herein, embodiments relate to a space-through charge transfer compound of

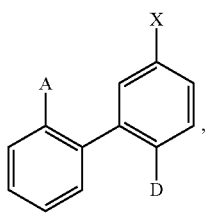

wherein A is selected from Formula 2, and D is selected from Formula 3:

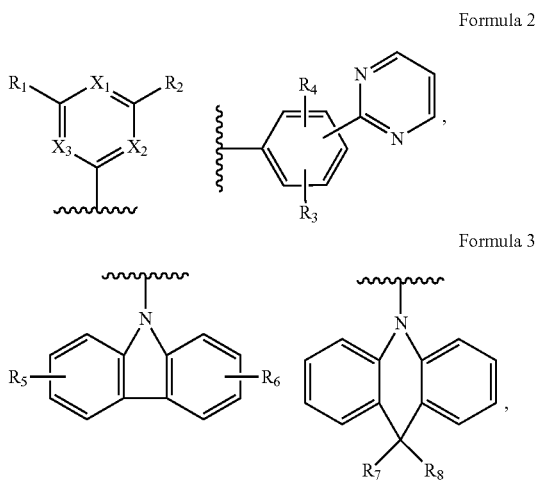

wherein each of X1, X2 and X3 is independently carbon or nitrogen, and at least one of X1, X2 and X3 is nitrogen, wherein each of R1 and R2 is independently selected from the group consisting of hydrogen, C1 to C10 alkyl group and C6 to C30 aryl group, and each of R3 and R4 is independently selected from the group consisting of hydrogen, cyano group and C1 to C10 alkyl group, and wherein each of R5 and R6 is independently selected from the group consisting of hydrogen and heteroaryl group, and each of R7 and R8 is hydrogen or R7 and R8 are bonded together to form a fused ring.

Embodiments also relate to an organic light emitting diode including a first electrode, a second electrode facing the first electrode, and a first emitting material layer between the first and second electrodes and including the space-through charge transfer compound.

Embodiments also relate to an organic light emitting display device including a substrate, the organic light emitting diode on the substrate; and an encapsulation film covering the organic light emitting diode.

It is to be understood that both the foregoing general description and the following detailed description are by example and explanatory and are intended to provide further explanation of the disclosure as claimed.

BRIEF DESCRIPTION OF THE SEVERAL VIEWS OF THE DRAWINGS

The accompanying drawings, which are included to provide a further understanding of the disclosure and are incorporated in and constitute a part of this specification, illustrate embodiments of the disclosure and together with the description serve to explain the principles of the disclosure.

DETAILED DESCRIPTION

Figure 1:
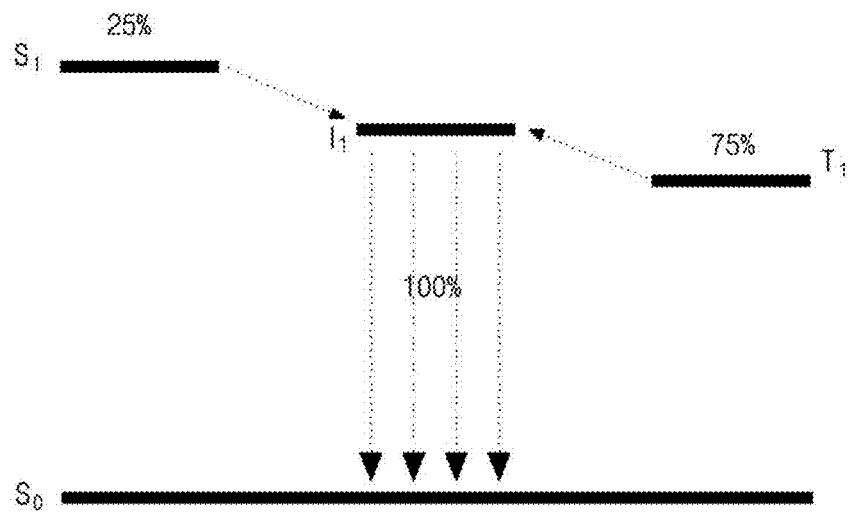
FIG. 1 is a view illustrating an emission mechanism of a space-through charge transfer compound according to the present disclosure.
Figure 2A:
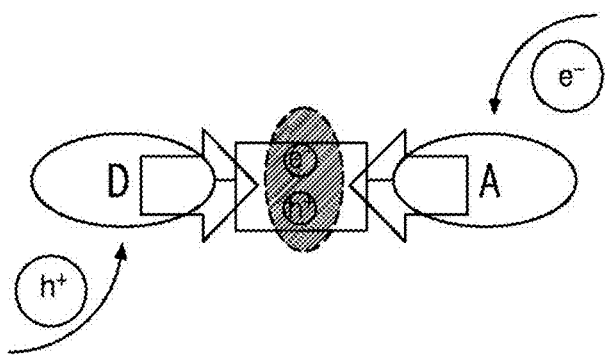
FIGS. 2A and 2B are views illustrating charge transfer in a space-through charge transfer compound according to the present disclosure.
Figure 2B:
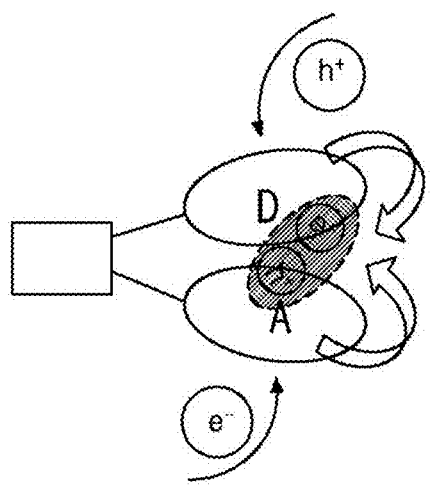

Reference will now be made in detail to example embodiments, examples of which are illustrated in the accompanying drawings.

A space-through charge transfer compound of the present disclosure has a biphenyl core (or bridge), an electron acceptor moiety, which is bonded (connected) to one of a 2-position of the biphenyl core and a 2'-position of the biphenyl core, and an electron donor moiety, which is bonded to the other one of a 2-position of the biphenyl core and a 2'-position of the biphenyl core. The space-through charge transfer compound may have Formula 1 of the following.

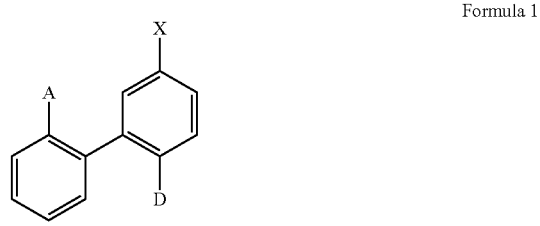

Formula 1

In the Formula 1, A as the electron acceptor moiety is selected from Formula 2.

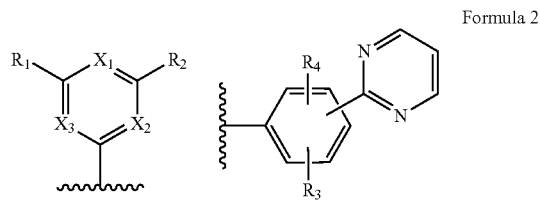

Formula 2

In the Formula 2, each of X1, X2 and X3 is independently carbon or nitrogen, and at least one of X1, X2 and X3 is nitrogen. In addition, each of R1 and R2 is independently selected from the group consisting of hydrogen, C1 to C10 alkyl group and C6 to C30 aryl group. For example, each of R1 and R2 may be phenyl. Each of R3 and R4 is independently selected from the group consisting of hydrogen, cyano group and C1 to C10 alkyl group.

For example, the electron acceptor moiety A may be selected from Formula 3.

Formula 3

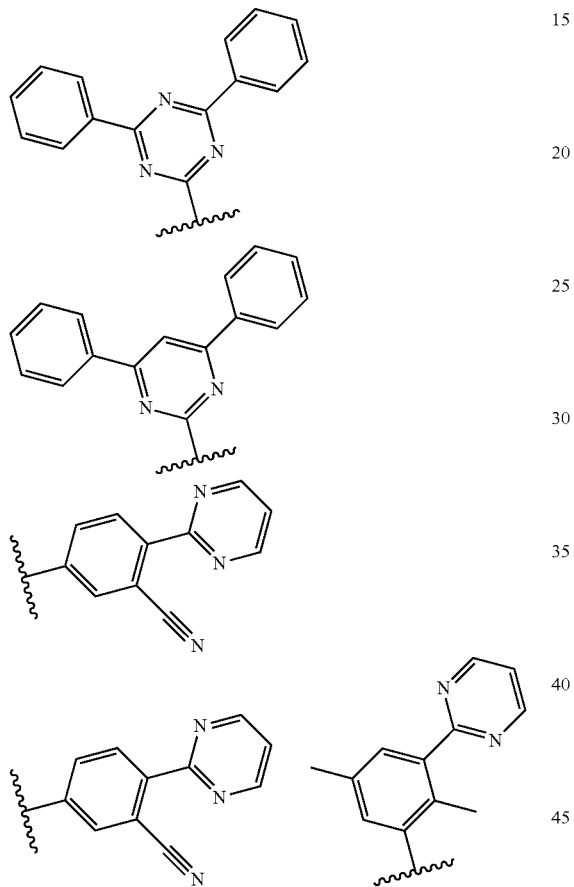

In the Formula 1, D as the electron donor moiety is selected from Formula 4.

Formula 4

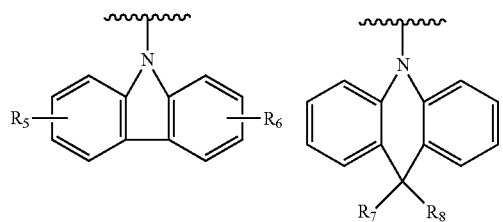

In the Formula 4, each of R5 and R6 is independently selected from the group consisting of hydrogen and heteroaryl group. For example, each of R5 and R6 may be carbazolyl. In addition, each of R7 and R8 is hydrogen or R7 and R8 are bonded together to form a fused ring.

For example, the electron donor moiety D may be selected from Formula 5.

Formula 5

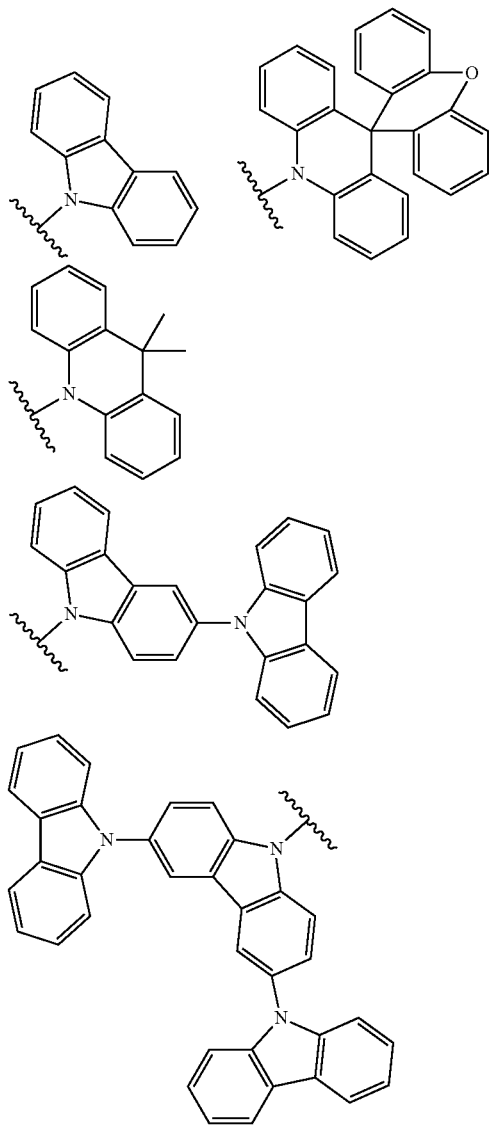

In the space-through charge transfer compound, the electron donor moiety and the electron acceptor moiety are bonded (combined or linked) in the molecule such that an overlap between the highest occupied molecular orbital (HOMO) and the lowest unoccupied molecular orbital (LUMO) is reduced. As a result, a charge transfer complex is generated, and the emitting efficiency of the space-through charge transfer compound is improved. Namely, in the space-through charge transfer compound, the triplet exciton is used for emission such that the emitting efficiency is improved.

In other words, since the space-through charge transfer compound of the present disclosure includes both of the electron donor moiety and the electron acceptor moiety, the charge is easily transferred in the molecule, and emission efficiency is improved.

In the space-through charge transfer compound of the present disclosure, since the electron donor moiety and the electron acceptor moiety are boned to the 2-position and the 2'-position of the biphenyl core, respectively, a gap or a distance between the electron donor moiety and the electron acceptor moiety is decreased or minimized. Accordingly, the charge transfer is directly generated through a space between the electron donor moiety and the electron acceptor moiety such that the conjugation length in the space-through charge transfer compound becomes shorter than another compound where the charge transfer is generated through a bonding orbital. As a result, a red shift problem in the emitted light can be prevented, and the space-through charge transfer compound of the present disclosure can provide deep blue emission.

Referring to FIG. 1, which is a view illustrating an emission mechanism of a space-through charge transfer compound according to the present disclosure, in the space-through charge transfer compound of the present disclosure, the triplet excitons as well as the singlet excitons are engaged in the emission such that the emitting efficiency is improved.

Namely, the triplet exciton is activated by a field or heat, and the triplet exciton and the singlet exciton are transferred into an intermediated state "$I_1$" and transited into a ground state "$S_O$" to emit the light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound or a thermally activated delayed fluorescence (TADF) compound.

In the related art fluorescence compound, since the HOMO and the LUMO are dispersed throughout an entirety of the molecule, the interconversion of the HOMO and the LUMO is impossible. (Selection Rule.)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety is spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound or the TADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit the light. As a result, the FADF compound has the theoretic quantum efficiency of 100%.

For example, the space-through charge transfer compound in Formula 1 may be one of compounds in Formula 6.

Formula 6

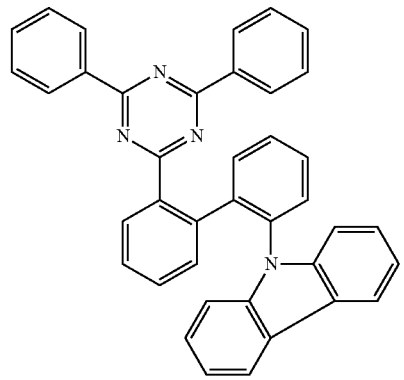

compound 1

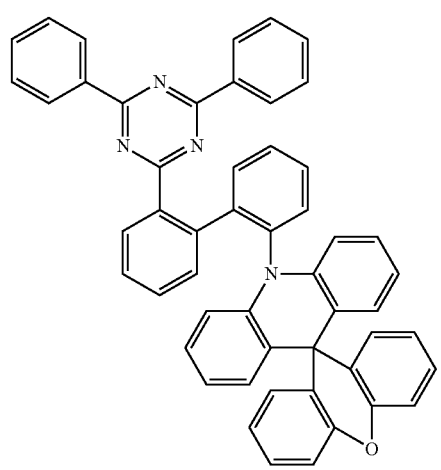

compound 2

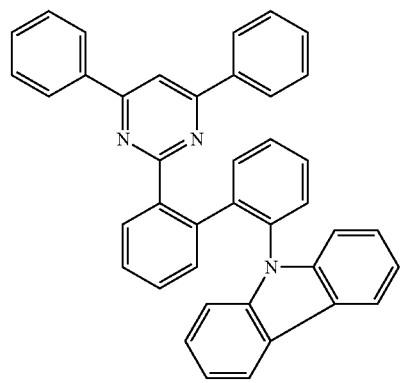

compound 3 compound 4
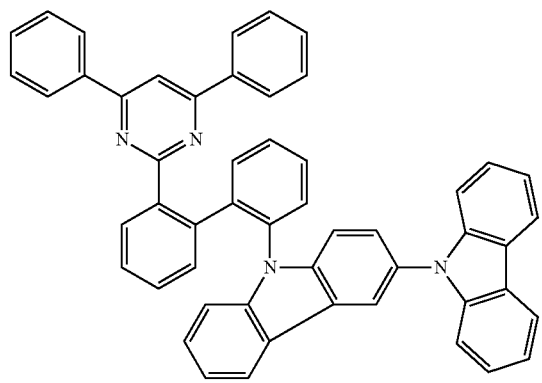
compound 5
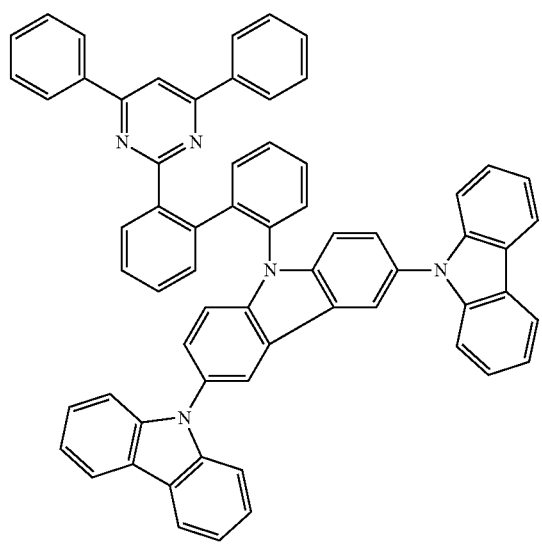
compound 6
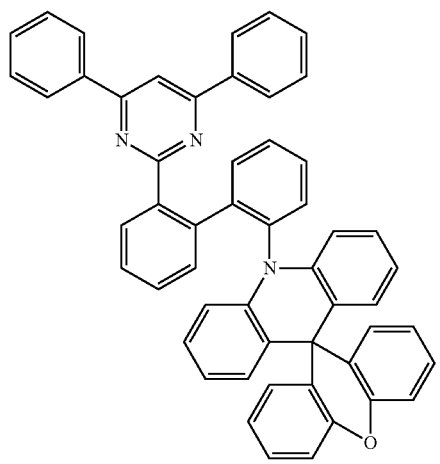
compound 7
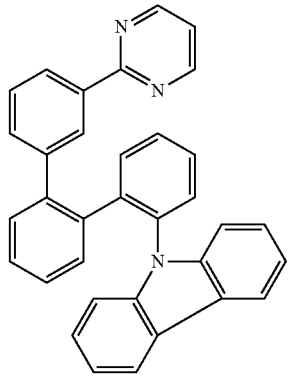
compound 8
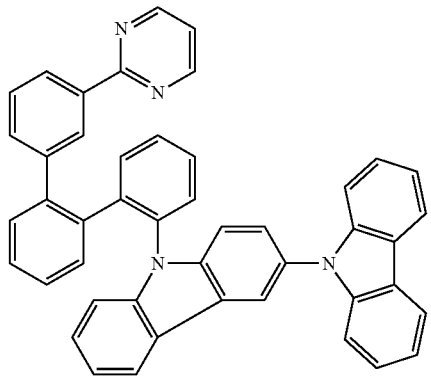
compound 9
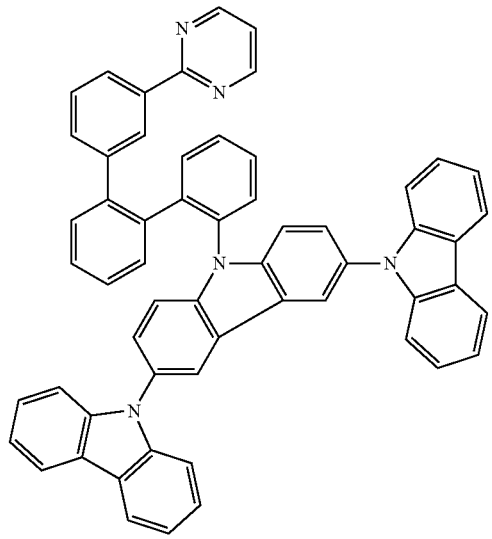

compound 10
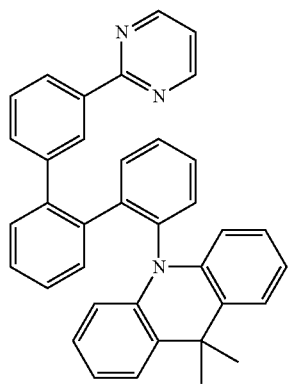
compound 11
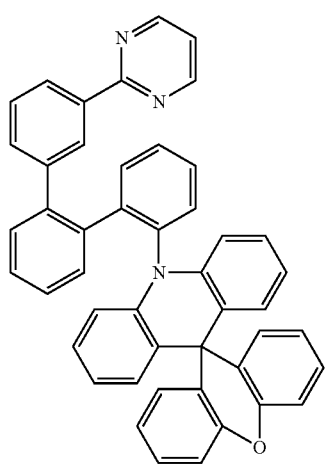
compound 12
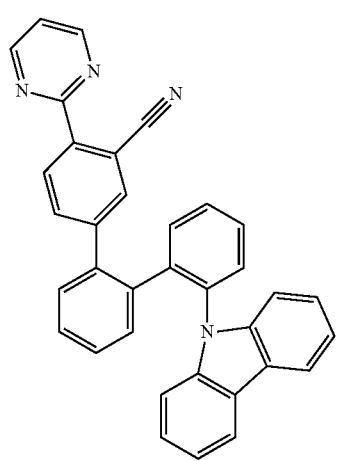
compound 13
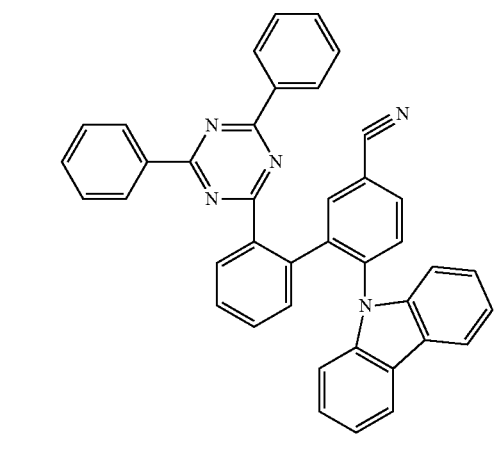
compound 14
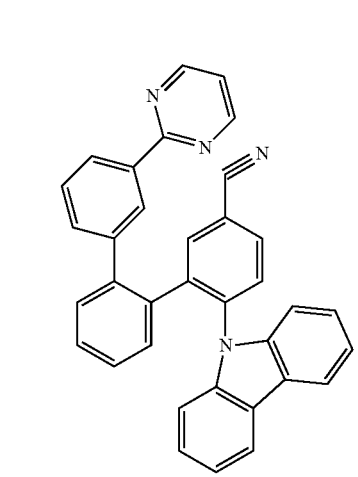
compound 15
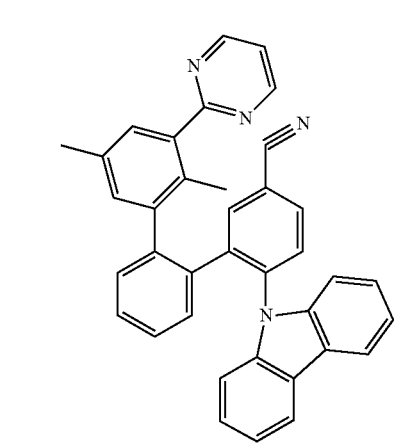

compound 16

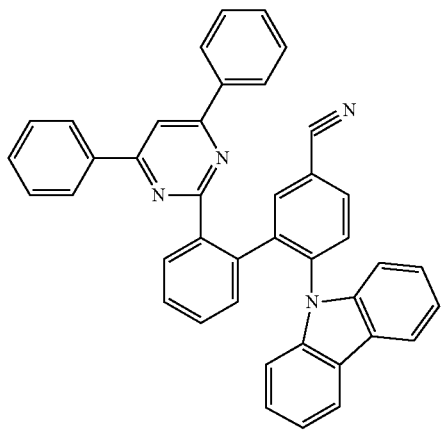

compound 17

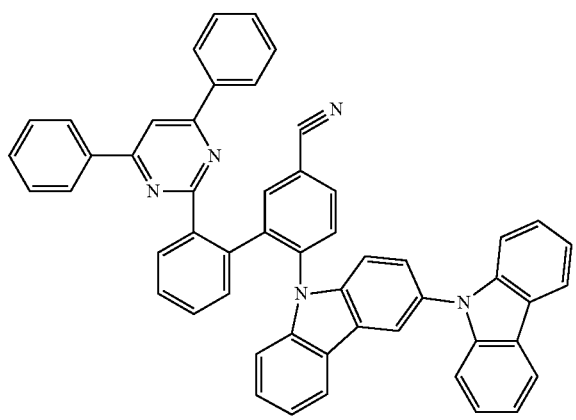

compound 18

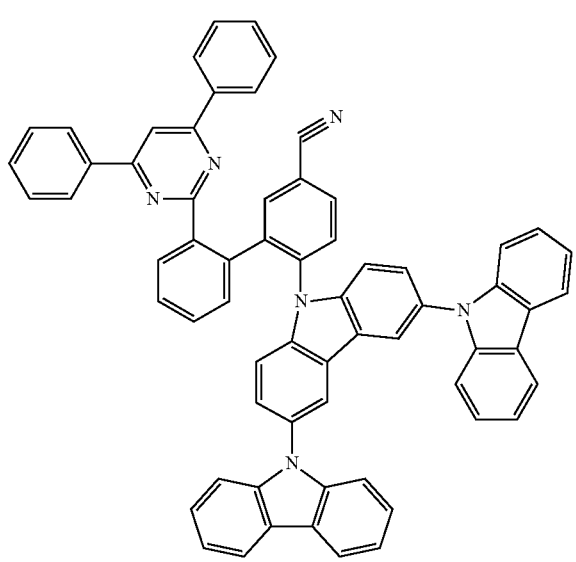

compound 19

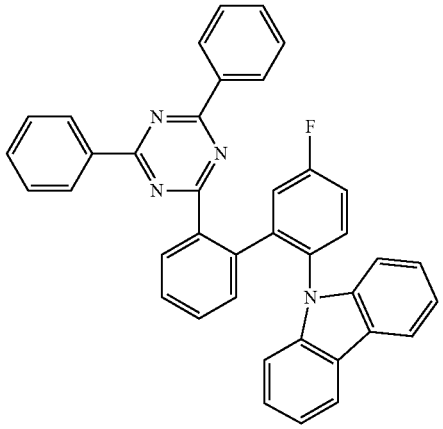

compound 20

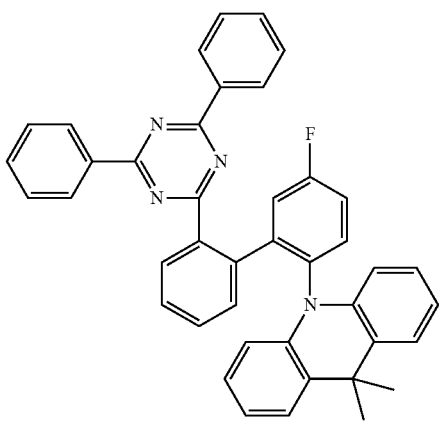

compound 21

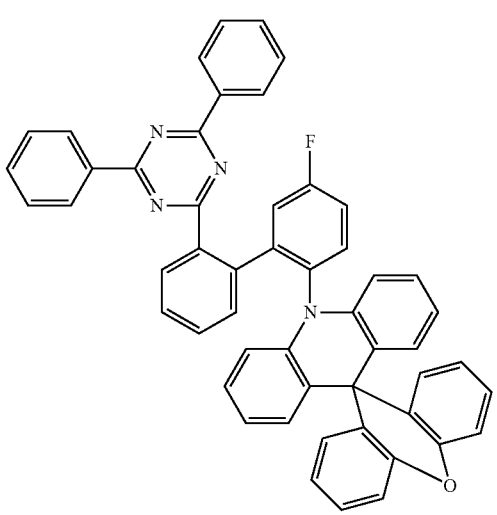

The space-through charge transfer compound of the present disclosure has a wide energy band gap such that the emission efficiency of the OLED using the compound is improved.

Figure 3A:
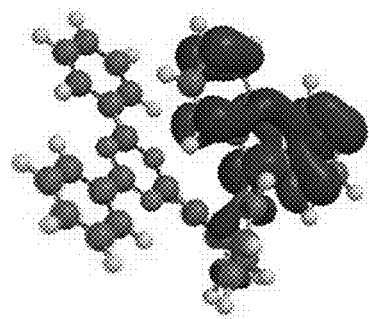
FIGS. 3A and 3B are views showing highest occupied molecular orbital (HOMO) distribution and lowest occupied molecular orbital (LUMO) distribution of a space-through charge transfer compound 1 according to the present disclosure.
Figure 3B:
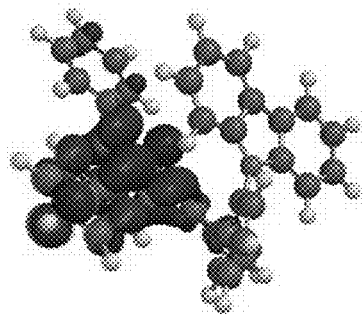
Figure 4A:
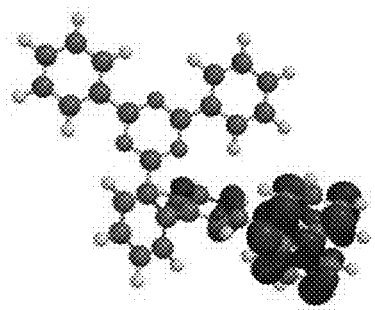
FIGS. 4A and 4B are views showing HOMO distribution and LUMO distribution of a comparative compound 1.
Figure 4B:
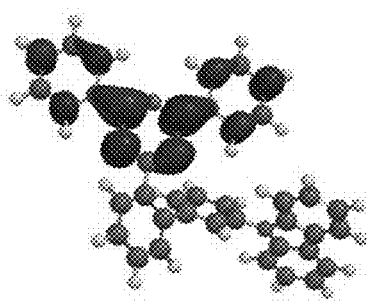
Figure 5A:
FIGS. 5A and 5B are views showing HOMO distribution and LUMO distribution of a space-through charge transfer compound 13 according to the present disclosure.
Figure 5B:
Figure 6A:
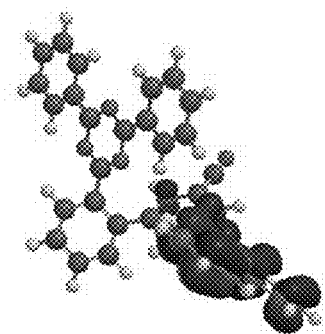
FIGS. 6A and 6B are views showing HOMO distribution and LUMO distribution of a comparative compound 2.
Figure 6B:
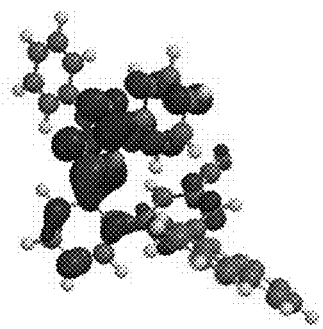

The HOMO distribution and the LUMO distribution of the compound 1 in the Formula 6 is shown in FIGS. 3A and 3B, and the HOMO distribution and the LUMO distribution of a comparative compound 1 of Formula 7 is shown in FIGS. 4A and 4B. The HOMO distribution and the LUMO distribution of the compound 13 in the Formula 6 is shown in FIGS. 5A and 5B, and the HOMO distribution and the LUMO distribution of a comparative compound 2 of Formula 8 is shown in FIGS. 6A and 6B. The energy level of HOMO, the energy level of LUMO and the energy bandgap (Eg) of the compounds 1 and 13 and the comparative compounds 1 and 2 are listed in Table 1.

Formula 7

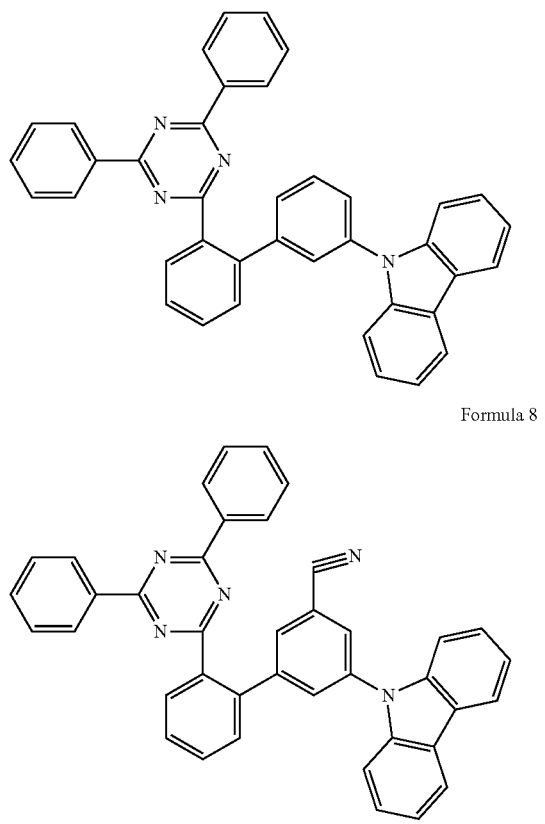

Formula 8

TABLE 1

|  | HOMO (eV) | LUMO (eV) | Eg |
|---|---|---|---|
| Compound 1 | 5.22 | 1.74 | 3.48 |
| Comparative compound 1 | 5.33 | 1.98 | 3.35 |
| Compound 13 | 5.52 | 1.92 | 3.6 |
| Comparative compound 2 | 5.60 | 2.14 | 3.46 |

As shown in FIGS. 3A to 6B and Table 1, in the space-through charge transfer compound of the present disclosure, the HOMO and the LUMO are easily separated, and the energy bandgap is increased in comparison to the comparative compounds. Accordingly, in the space-through charge transfer compound of the present disclosure, the triplet exciton is engaged in the emission such that the emitting efficiency is improved and the deep blue emission is provided.

Synthesis

Synthesis of Compound 1

Reaction Formula 1-1

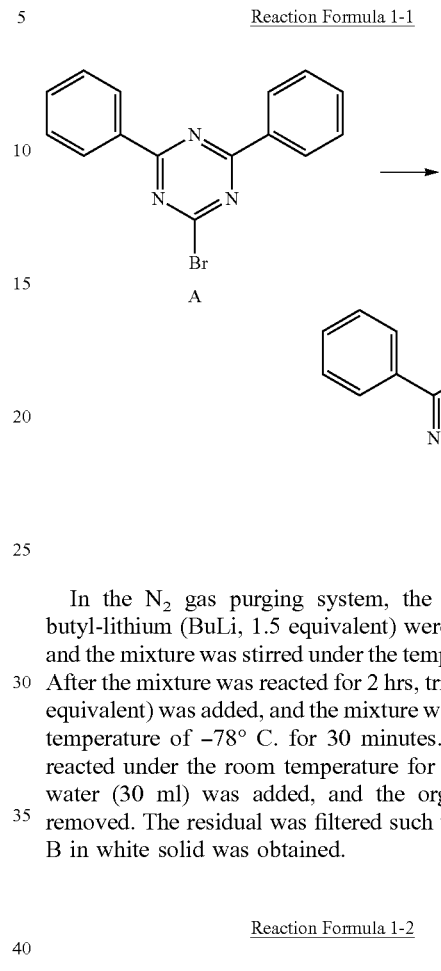

In the N₂ gas purging system, the compound A and butyl-lithium (BuLi, 1.5 equivalent) were added into ether, and the mixture was stirred under the temperature of −78° C. After the mixture was reacted for 2 hrs, trimethyl borate (1.2 equivalent) was added, and the mixture was stirred under the temperature of −78° C. for 30 minutes. The mixture was reacted under the room temperature for 14 hrs. HCl in DI water (30 ml) was added, and the organic solvent was removed. The residual was filtered such that the compound B in white solid was obtained.

Reaction Formula 1-2

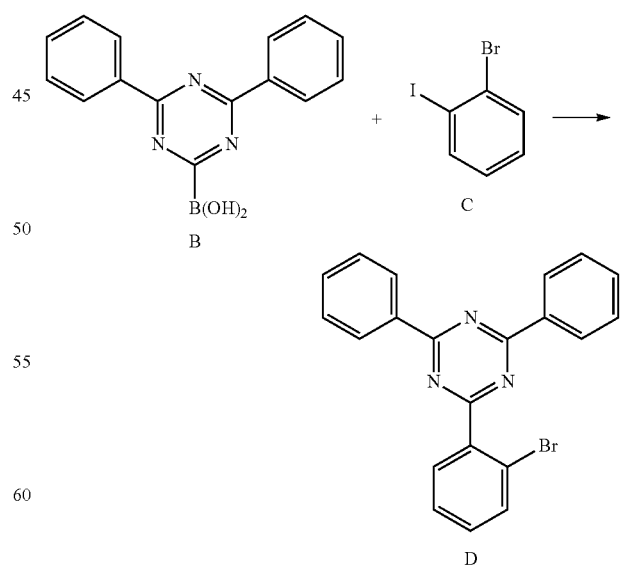

In the N₂ gas purging system, the compound B, the compound C (0.6 equivalent), Pd(0) (0.1 equivalent) and potassium carbonate (4.0 equivalent) was added in toluene, and the mixture was stirred in the oil bath under the temperature of 80° C. for 34 hrs. Water was added into the mixture and was extracted. The column chromatography using the developing solvent of hexane and methylenechloride (7:1) is performed such that the compound D of white solid was obtained.

Reaction Formula 1-3

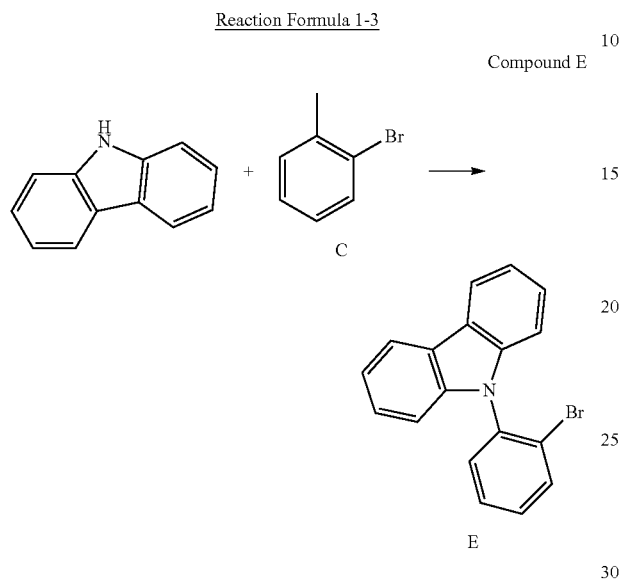

In the N$_2$ gas purging system, carbazole, the compound C (0.5 equivalent), CuI (0.1 equivalent), diaminocyclohexane (3.5 equivalent) and potassium phosphate (4.0 equivalent) were added in 1,4-dioxane, and the mixture was stirred in the oil bath under the temperature of 90° C. for 12 hrs. Water was added into the mixture and was extracted. The column chromatography using the developing solvent of hexane and methylenechloride (9:1) is performed such that the compound E of white solid was obtained.

Reaction Formula 1-4

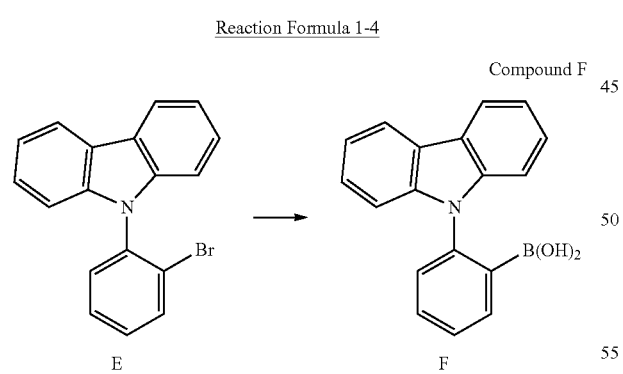

In the N$_2$ gas purging system, the compound E and BuLi (1.5 equivalent) were added into ether, and the mixture was stirred under the temperature of −78° C. After the mixture was reacted for 2 hrs, trimethyl borate (1.2 equivalent) was added, and the mixture was stirred under the temperature of −78° C. for 30 minutes. The mixture was reacted under the room temperature for 24 hrs. HCl in DI water (30 ml) was added, and the organic solvent was removed. The residual was filtered such that the compound F in white solid was obtained.

Reaction Formula 1-5

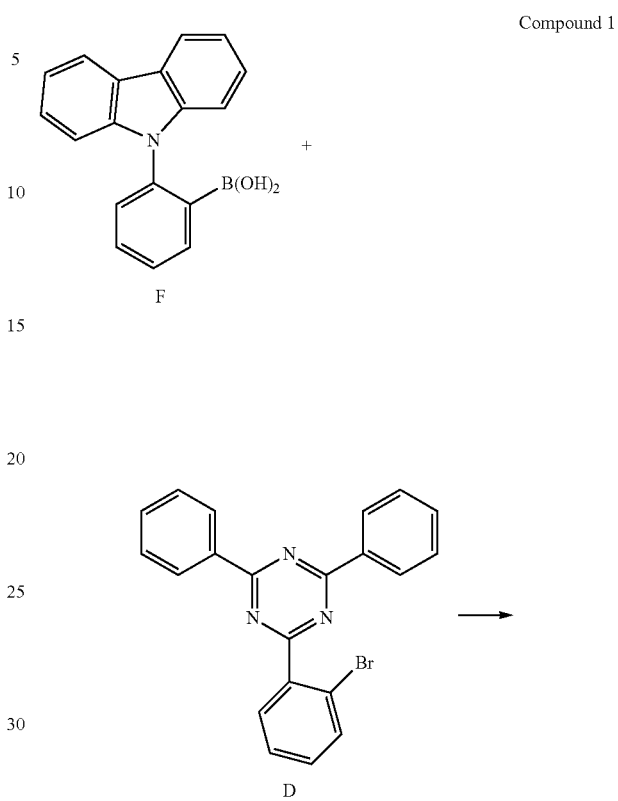

In the N$_2$ gas purging system, the compound F, the compound D (1.3 equivalent), Pd(0) (0.1 equivalent) and potassium carbonate (4.0 equivalent) was added in toluene, and the mixture was stirred in the oil bath under the temperature of 80° C. for 48 hrs. Water was added into the mixture and was extracted. The column chromatography using the developing solvent of hexane and methylenechloride (9.5:0.5) is performed such that the compound 1 of white solid was obtained.

Synthesis of Compound 13

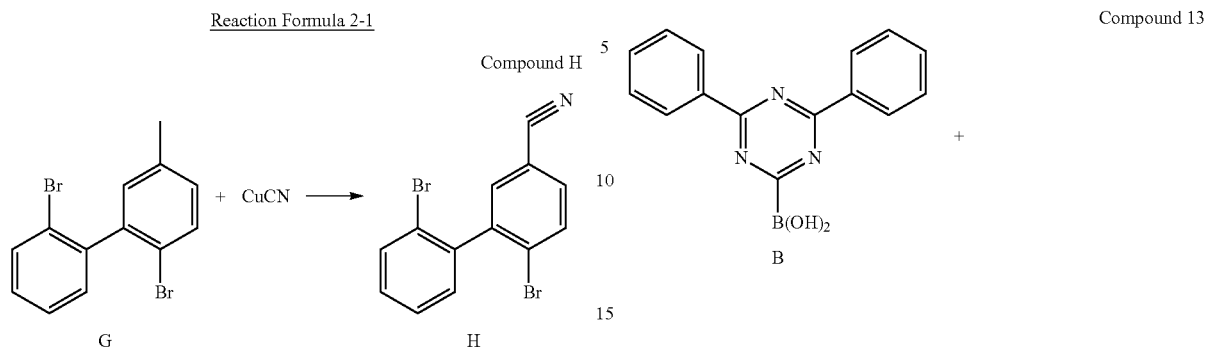

Reaction Formula 2-1

Compound H

G + CuCN → H

In the N₂ gas purging system, the compound G and CuCN (1.5 equivalent) were added into dimethylformamide (DMF), and the mixture was stirred under the temperature of 150° C. for 48 hrs. The mixture was slowly added into the iced water of 0° C. and was stirred for 30 minutes. Ammonia aqueous solution was added and extracted. The solvent was removed, and the resultant was absorbed by silica. The column chromatography using the developing solvent of methylenechloride and hexane (1:1) is performed such that the compound H of solid was obtained.

Reaction Formula 2-2

Compound I

H + carbazole → I

In the N₂ gas purging system, the compound H, carbazole (0.5 equivalent), CuI (0.1 equivalent), diaminocyclohexane (3.5 equivalent) and potassium phosphate (4.0 equivalent) were added in 1,4-dioxane, and the mixture was stirred in the oil bath under the temperature of 90° C. for 24 hrs. Water was added into the mixture and was extracted. The column chromatography using the developing solvent of hexane and ethylacetate (7:1) is performed such that the compound I of white solid was obtained.

Reaction Formula 2-3

Compound 13

B + I → compound 13

In the N₂ gas purging system, the compound B, the compound I (1.3 equivalent), Pd(0) (0.1 equivalent) and potassium carbonate (4.0 equivalent) was added in toluene, and the mixture was stirred in the oil bath under the temperature of 80° C. for 50 hrs. Water was added into the mixture and was extracted. The column chromatography using the developing solvent of hexane and ethylacetate (6:1) is performed such that the compound 13 of white solid was obtained.

Synthesis of Compound 8

Reaction Formula 3-1

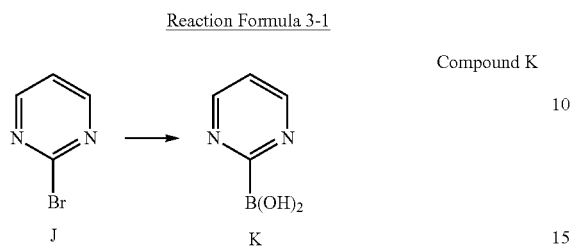

In the $N_2$ gas purging system, the compound J and BuLi (1.5 equivalent) were added into ether, and the mixture was stirred under the temperature of −78° C. After the mixture was reacted for 1 hr, triethyl borate (1.2 equivalent) was added, and the mixture was stirred under the temperature of −78° C. for 30 minutes. The mixture was reacted under the room temperature for 12 hrs. HCl in DI water (30 ml) was added, and the organic solvent was removed. The residual was filtered such that the compound K in white solid was obtained.

Reaction Formula 3-2

Compound M

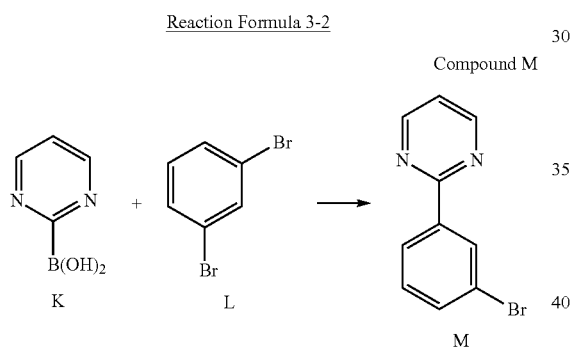

In the $N_2$ gas purging system, the compound K, the compound L (0.5 equivalent), CuI (0.1 equivalent), diaminocyclohexane (3.5 equivalent) and potassium phosphate (4.0 equivalent) were added in 1,4-dioxane, and the mixture was stirred in the oil bath under the temperature of 60° C. for 24 hrs. Water was added into the mixture and was extracted. The column chromatography using the developing solvent of hexane and methylenechloride (9:1) is performed such that the compound M of white solid was obtained.

Reaction Formula 3-3

Compound O

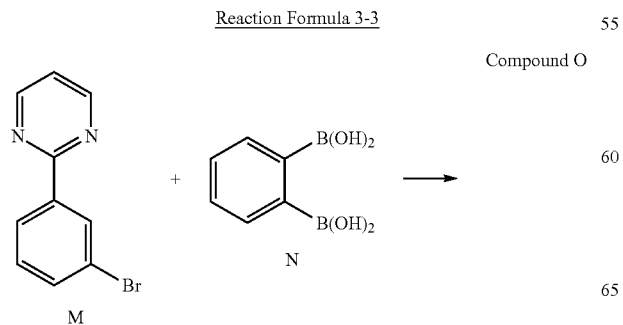

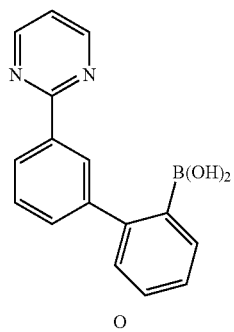

In the $N_2$ gas purging system, the compound M, the compound N (0.6 equivalent), Pd(0) (0.1 equivalent) and potassium carbonate (4.0 equivalent) was added in toluene, and the mixture was stirred in the oil bath under the temperature of 80° C. for 12 hrs. Water was added into the mixture and was extracted. The solvent was evaporated such that the compound O of yellow solid was obtained.

Reaction Formula 3-4

Compound Q

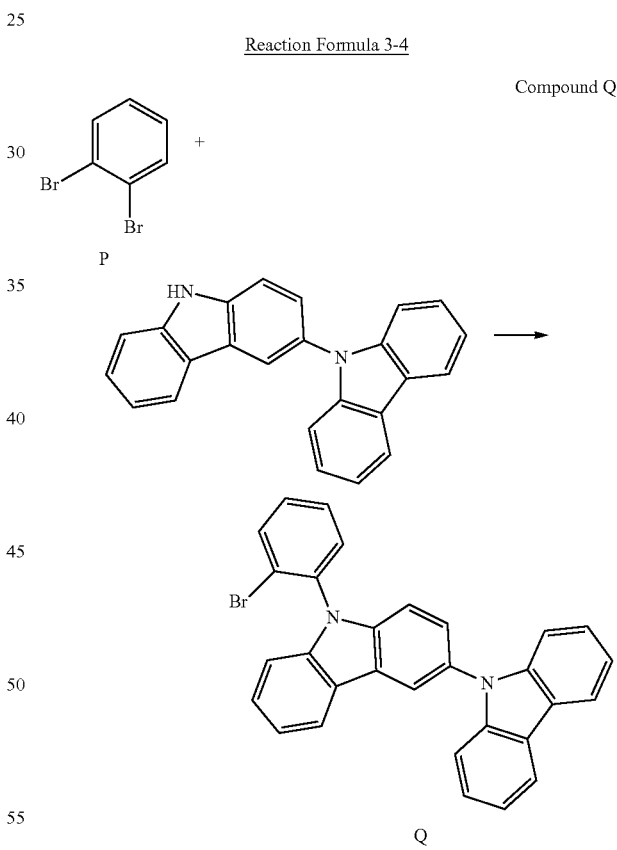

In the $N_2$ gas purging system, the compound P, bicarbazole (0.45 equivalent), CuI (0.1 equivalent), diaminocyclohexane (3.5 equivalent) and potassium phosphate (4.0 equivalent) were added in 1,4-dioxane, and the mixture was stirred in the oil bath under the temperature of 60° C. for 14 hrs. Water was added into the mixture and was extracted. The column chromatography using the developing solvent of hexane and methylenechloride (10:1) is performed such that the compound Q of white solid was obtained.

Reaction Formula 3-5

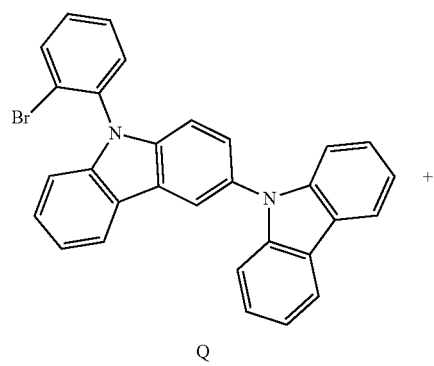

Compound 8

Q

+

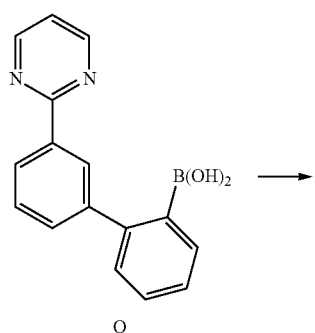

O

↓

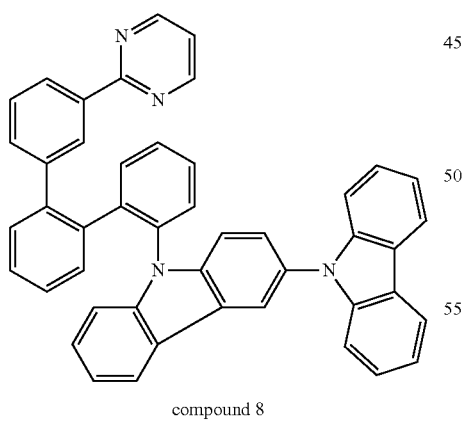

compound 8

In the $N_2$ gas purging system, the compound Q, the compound O (1.3 equivalent), Pd(0) (0.1 equivalent) and potassium carbonate (4.0 equivalent) was added in toluene, and the mixture was stirred in the oil bath under the temperature of 100° C. for 24 hrs. Water was added into the mixture and was extracted. The column chromatography using the developing solvent of hexane and methylenechloride (5:1) is performed such that the compound 8 of white solid was obtained.

Synthesis of Compound 19

Reaction Formula 4-1

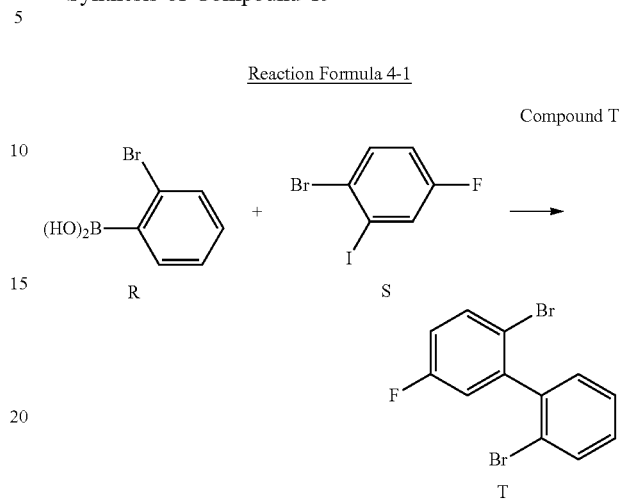

Compound T

R        S

T

In the $N_2$ gas purging system, the compound R, the compound S (1.0 equivalent), Pd(0) (0.1 equivalent) and potassium carbonate (4.0 equivalent) was added in toluene, and the mixture was stirred in the oil bath under the temperature of 80° C. for 18 hrs. Water was added into the mixture and was extracted. The column chromatography using the developing solvent of hexane and methylenechloride (9:1) is performed such that the compound T of white solid was obtained.

Reaction Formula 4-2

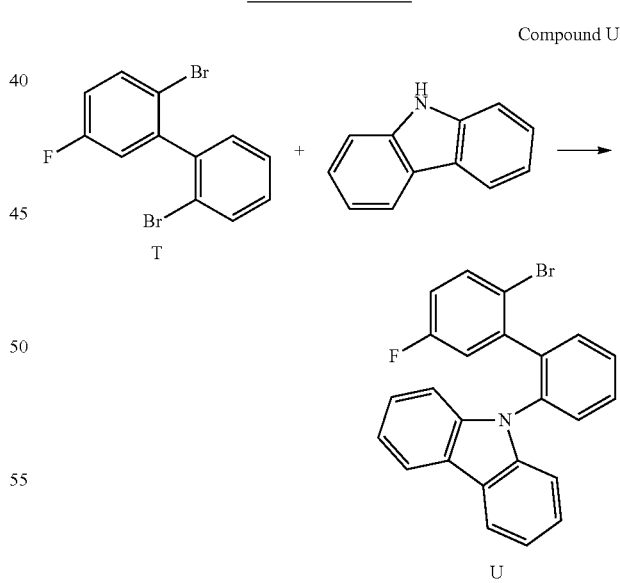

Compound U

T

U

In the $N_2$ gas purging system, the compound T, carbazole (0.5 equivalent), CuI (0.1 equivalent), diaminocyclohexane (3.5 equivalent) and potassium phosphate (4.0 equivalent) were added in 1,4-dioxane, and the mixture was stirred in the oil bath under the temperature of 80° C. for 12 hrs. Water was added into the mixture and was extracted. The column chromatography using the developing solvent of hexane and methylenechloride (9:1) is performed such that the compound U of white solid was obtained.

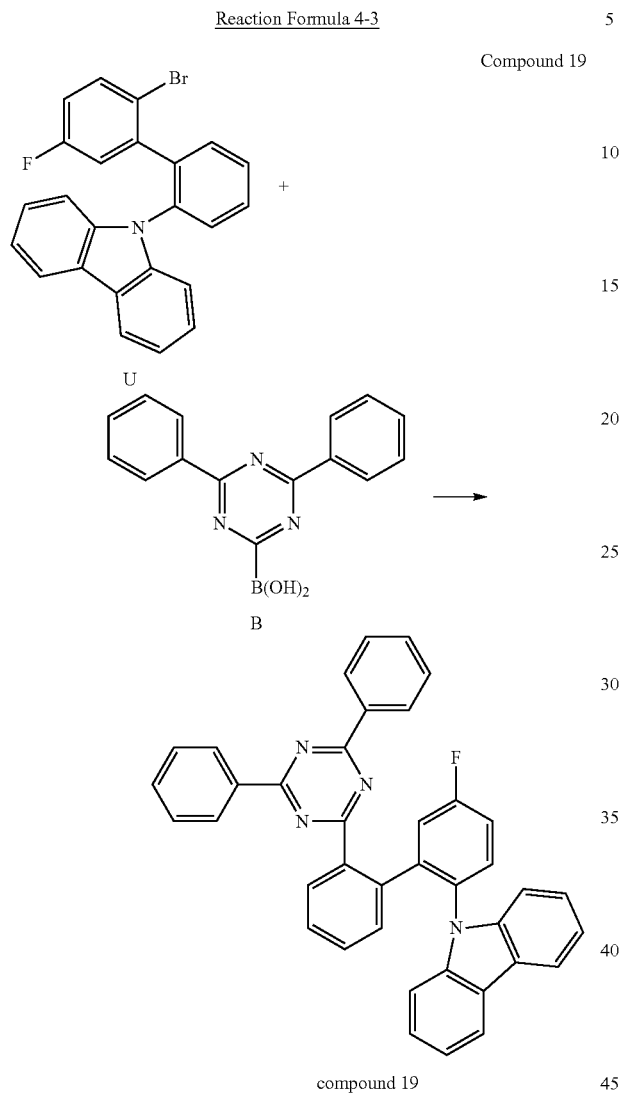

Reaction Formula 4-3

Compound 19 compound 19

In the N$_2$ gas purging system, the compound U, the compound B (1.4 equivalent), Pd(0) (0.15 equivalent) and potassium carbonate (4.0 equivalent) was added in toluene, and the mixture was stirred in the oil bath under the temperature of 100° C. for 24 hrs. Water was added into the mixture and was extracted. The column chromatography using the developing solvent of hexane and methylenechloride (8:1) is performed such that the compound 19 of white solid was obtained.

In the space-through charge transfer compound of the present disclosure, the 25% excitons in the singlet state and the 75% excitons in the triplet state are transited into the intermediate state by an outer force, i.e., a field generated when the OLED is driven. (Intersystem crossing.) The excitons in the intermediate state are transited into the ground state such that the emitting efficiency is improved. Namely, in the fluorescent compound, since the singlet exciton and the triplet exciton are engaged in emission, the emitting efficiency is improved.

OLED

An ITO layer is deposited on a substrate and washed to form an anode (3 mm*3 mm). The substrate is loaded in a vacuum chamber, and a hole injecting layer, a hole transporting layer, an emitting material layer, an electron transporting layer, an electron injecting layer, and a cathode (Al) are sequentially formed on the anode under a base pressure of about $10^{-6}$ to $10^{-7}$ Torr. The emitting material layer is formed using a host of a material in Formula 9 and a dopant (30 wt %).

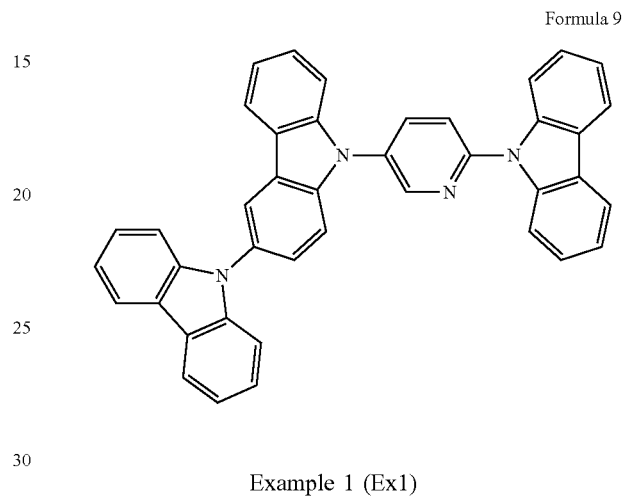

Formula 9

Example 1 (Ex1)

The compound 1 in Formula 6 is used as the dopant in the emitting material layer.

Example 2 (Ex2)

The compound 13 in Formula 6 is used as the dopant in the emitting material layer.

Example 3 (Ex3)

The compound 8 in Formula 6 is used as the dopant in the emitting material layer.

Example 4 (Ex4)

The compound 19 in Formula 6 is used as the dopant in the emitting material layer.

Comparative Example 1 (Ref1)

The compound in Formula 7 is used as the dopant in the emitting material layer.

Comparative Example 2 (Ref2)

The compound in Formula 8 is used as the dopant in the emitting material layer.

The properties, i.e., a PL maximum value (PL$_{max}$, nm), an extinction time of an emitting exciton (Tau, μs), voltate (V), current efficiency (cd/A), power efficiency (lm/W), external quantum efficiency (EQE, %), color coordinate index (CIE (X), CIE(Y)), lifespan (T95, hr), of the OLED in Examples 1 to 4 and Comparative Examples 1 and 2 are measured and listed in Table 2. The lifespan is a time taking the brightness from the initial brightness (300 nit) into 95%.

TABLE 2

| | PL$_{max}$ | Tau | V | cd/A | lm/W | EQE | CIE (X) | CIE (Y) | T95 |
|---|---|---|---|---|---|---|---|---|---|
| Ex1 | 458 | 3.6 | 4.02 | 23.71 | 18.52 | 15.09 | 0.152 | 0.196 | 57 |
| Ex2 | 462 | 5.8 | 3.98 | 25.33 | 19.98 | 16.31 | 0.157 | 0.207 | 52 |
| Ex3 | 452 | 3.9 | 3.88 | 22.86 | 18.50 | 14.76 | 0.151 | 0.185 | 50 |
| Ex4 | 450 | 2.4 | 3.89 | 21.74 | 17.55 | 14.45 | 0.150 | 0.182 | 45 |
| Ref1 | 475 | 1.3 | 3.94 | 18.49 | 14.73 | 12.52 | 0.152 | 0.251 | 7.0 |
| Ref2 | 477 | 2.1 | 3.80 | 18.68 | 15.43 | 12.78 | 0.156 | 0.263 | 5.8 |

As shown in Table 2, in comparison to the OLED of Comparative Examples 1 and 2, the OLED including the space-through charge transfer compound of the present disclosure has high emitting efficiency and long lifespan and provides a deep blue emission.

For example, the compounds 1 and 13 of Formula 6 and the comparative compounds 1 and 2 of Formulas 7 and 8 have a difference in a bonding position of the electron donor moiety, and a distance between the electron acceptor moiety and the electron donor moiety in the compounds 1 and 13 is decreased. Accordingly, the charge transfer property through a space between the electron donor moiety and the electron acceptor moiety is improved such that the space-through charge transfer compound of the present disclosure has advantages of high emitting efficiency, long lifespan and deep blue emission.

In addition, since the extinction time of the emitting exciton is several micro seconds, the space-through charge transfer compound of the present disclosure has a delayed fluorescence property. General fluorescence material has the extinction time of several nano-seconds.

Figure 7:
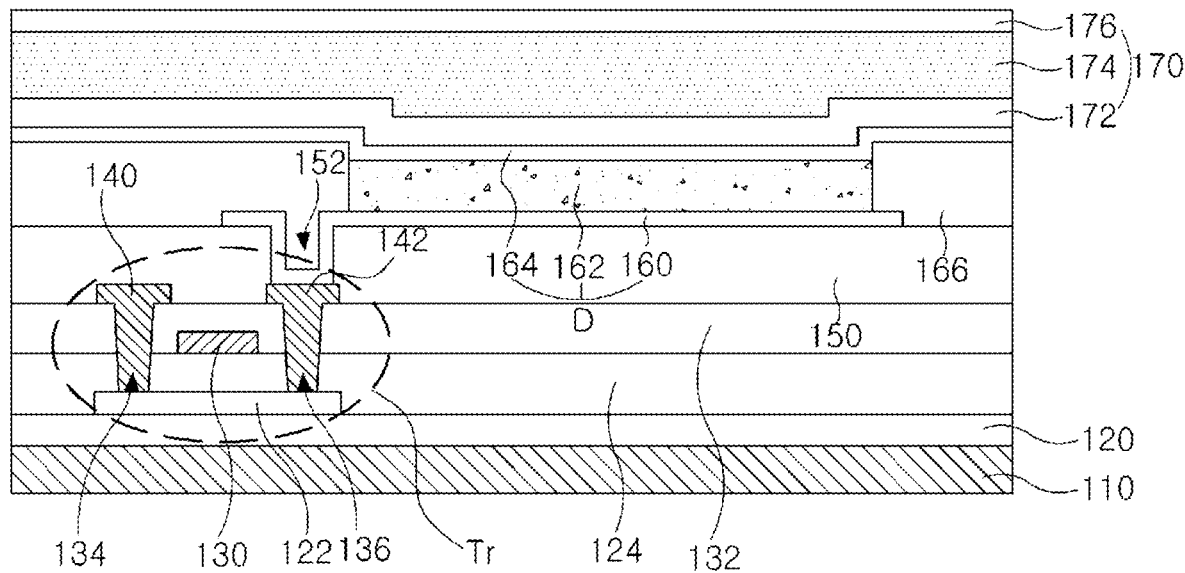
FIG. 7 is a schematic cross-sectional view of an organic light emitting display device according to the present disclosure.

FIG. 7 is a schematic cross-sectional view of an organic light emitting display device according to the present disclosure.

As shown in FIG. 7, the OLED device 100 includes a substrate 110, a TFT Tr and an organic light emitting diode D connected to the TFT Tr.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 7, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 includes the space-through charge transfer compound of Formula 1. The space-through charge transfer compound may be used as a dopant, and the organic emitting layer 162 may further include a host. For example, the dopant may have a weight % of about 1 to 30 with respect to the host. The organic emitting layer 162 provides blue light.

The organic emitting layer 162 may have a single-layered structure of an emitting material layer including an emitting material. To increase an emitting efficiency of the OLED device, the organic emitting layer 162 may have a multi-layered structure.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy.

The first electrode 160, the organic emitting layer 162 and the second electrode 164 constitute the organic light emitting diode D.

An encapsulation film 170 is formed on the second electrode 164 to prevent penetration of moisture into the organic light emitting diode D. The encapsulation film 170 includes a first inorganic insulating layer 172, an organic insulating layer 174 and a second inorganic insulating layer 176 sequentially stacked, but it is not limited thereto.

A polarization plate (not shown) for reducing an ambient light reflection may be disposed over the top-emission type organic light emitting diode D. For example, the polarization plate may be a circular polarization plate.

In addition, a cover window (not shown) may be attached to the encapsulation film 170 or the polarization plate. In this instance, the substrate 110 and the cover window have a flexible property such that a flexible OLED device may be provided.

Figure 8:
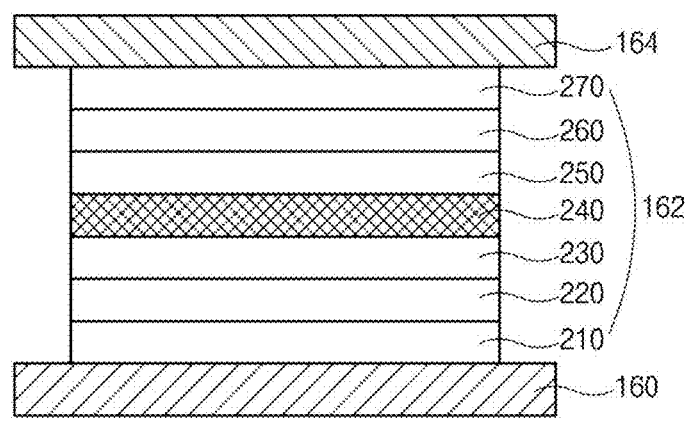
FIG. 8 is a schematic cross-sectional view of an organic light emitting diode (OLED) according to the present disclosure.

FIG. 8 is a schematic cross-sectional view of an organic light emitting diode (OLED) according to the present disclosure.

As shown in FIG. 8, the organic light emitting diode D includes the first and second electrodes 160 and 164, which face each other, and the organic emitting layer 162 therebetween. The organic emitting layer 162 includes an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

The EML 240 includes the space-through charge transfer compound of Formula 1 as a dopant and may further include a host.

A difference between an energy level of the HOMO of the host "$HOMO_{Host}$" and an energy level of the HOMO of the dopant "$HOMO_{Dopant}$" or a difference between an energy level of the LUMO of the host "$LUMO_{Host}$" and an energy level of the LUMO of the dopant "$LUMO_{Dopant}$" is less than about 0.5 eV. In this instance, the charge transfer efficiency from the host to the dopant may be improved.

The energy level of triplet state of the dopant is smaller than the energy level of triplet state of the host, and a difference between the energy level of singlet state of the dopant and the energy level of triplet state of the dopant is less than 0.3 eV. ($\Delta E_{ST} \leq 0.3$ eV.) As the difference "$\Delta E_{ST}$" is smaller, the emitting efficiency is higher. In addition, even if the difference "$\Delta E_{ST}$" between the energy level of singlet state of the dopant and the energy level of triplet state of the dopant is about 0.3 eV, which is relatively large, the excitons in the singlet state and the excitons in the triplet state can be transited into the intermediate state.

For example, the host, which meets the above condition, may be selected from materials in Formula 10. (Bis[2-(diphenylphosphino)phenyl]ether oxide (DPEPO), 2,8-bis (diphenylphosphoryl)dibenzothiophene (PPT), 2,8-di(9H-carbazol-9-yl)dibenzothiophene (DCzDBT), m-bis (carbazol-9-yl)biphenyl (m-CBP), Diphenyl-4-triphenyl silylphenyl-phosphine oxide (TPSO1), 9-(9-phenyl-9H-carbazol-6-yl)-9H-carbazole (CCP) in order.)

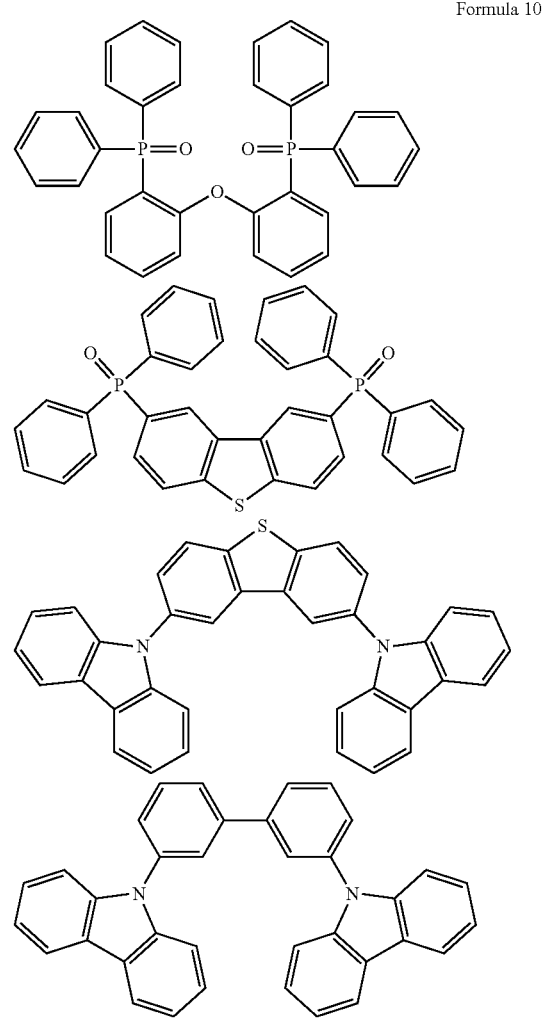

Formula 10

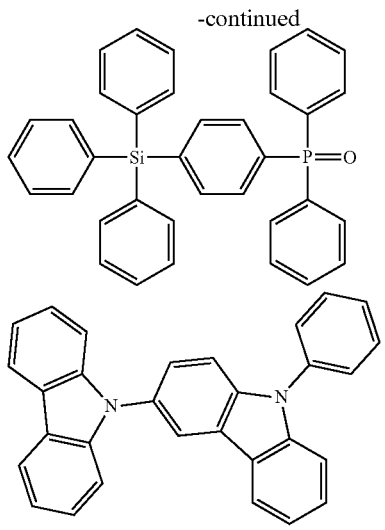

On the other hand, the space-through charge transfer compound of the present disclosure may act as a host in the EML 240, and the EML 240 may further include a dopant to emit the blue light. In this instance, the dopant has about 1 to 30 weight % with respect to the host. Since the development of the blue host having excellent properties is insufficient, the space-through charge transfer compound of the present disclosure may be used as the host to increase the degree of freedom for the host. In this instance, the energy level of triplet state of the dopant may be smaller than the energy level of triplet state of the host of the space-through charge transfer compound of the present disclosure.

The EML 240 may include a first dopant of the space-through charge transfer compound of the present disclosure, a host, and a second dopant. The weight % summation of the first and second dopants may be about 1 to 30 to emit the blue light. The second dopant may be a fluorescence material (compound). In this instance, the emitting efficiency and the color purity may be further improved.

An energy level of singlet state of the first dopant (the space-through charge transfer compound) is greater than that of the second dopant. An energy level of triplet state of the first dopant is smaller than that of the host and greater than that of the second dopant.

In this instance, the energy level of triplet state of the first dopant, i.e., the space-through charge transfer compound of the present disclosure, may be smaller than the energy level of triplet state of the host and larger than the energy level of triplet state of the second dopant. In addition, a difference between the energy level of singlet state of the first dopant and the energy level of triplet state of the first dopant is less than 0.3 eV. ($\Delta E_{ST} \leq 0.3$ eV) As the difference "$\Delta E_{ST}$" is smaller, the emitting efficiency is higher. In the space-through charge transfer compound of the present disclosure, even if the difference "$\Delta E_{ST}$" between the energy level of singlet state of the dopant and the energy level of triplet state of the dopant is about 0.3 eV, which is relatively large, the excitons in the singlet state "$S_1$" and the excitons in the triplet state "$T_1$" can be transited into the intermediate state "$I_1$".

As mentioned above, in the space-through charge transfer compound of the present disclosure, since the electron donor moiety and the electron acceptor moiety are bonded to the biphenyl core in one molecule and the overlap between the HOMO and the LUMO is decreased, the space-through charge transfer compound of the present disclosure acts as a charge transfer complex such that the emitting efficiency of the compound is improved. Namely, in the space-through charge transfer compound of the present disclosure, the excitons in the triplet state are engaged in the emission such that the emitting efficiency of the compound is improved.

Since the electron donor moiety and the electron acceptor moiety are boned to the 2-position and the 2'-position of the biphenyl core, respectively, a gap or a distance between the electron donor moiety and the electron acceptor moiety is decreased or minimized. Accordingly, the charge transfer is directly generated through a space between the electron donor moiety and the electron acceptor moiety such that the conjugation length in the space-through charge transfer compound becomes shorter than another compound where the charge transfer is generated through a bonding orbital. As a result, a red shift problem in the emitted light can be prevented, and the space-through charge transfer compound of the present disclosure can provide deep blue emission.

As a result, the OLED and the organic light emitting display device including the space-through charge transfer compound has high emitting efficiency and lifespan and provides high quality image.

Figure 9:
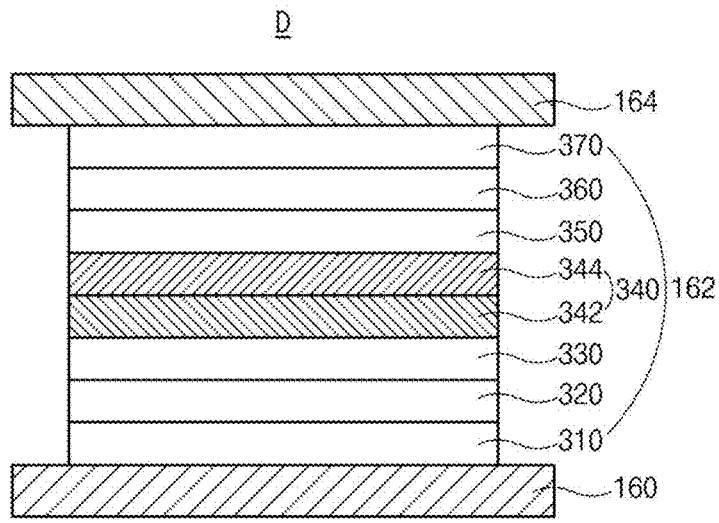
FIG. 9 is a schematic cross-sectional view of an organic light emitting diode (OLED) according to the present disclosure.

FIG. 9 is a schematic cross-sectional view of an organic light emitting diode (OLED) according to the present disclosure.

As shown in FIG. 9, an organic light emitting diode D includes the first and second electrodes 160 and 164, which face each other, and the organic emitting layer 162 therebetween. The organic emitting layer 162 includes an EML 340, which includes first and second layers 342 and 344 and is positioned between the first and second electrodes 160 and 164, a HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

In the EML 340, one of the first and second layers 342 and 344 includes the space-through charge transfer compound of the present disclosure as a dopant, and the other one of the first and second layers 342 and 344 includes a fluorescence material as a dopant. An energy level of singlet state of the space-through charge transfer compound is greater than that of the fluorescence material.

The organic light emitting diode, where the first layer 342 includes the space-through charge transfer compound and the second layer 344 includes the fluorescent dopant, will be explained.

In the organic light emitting diode D, the energy level of singlet state and the energy level of triplet state of the space-through charge transfer compound are transferred into the fluorescence material such that the emission is generated from the fluorescence material. Accordingly, the quantum efficiency of the organic light emitting diode D is increased, and the full width at half maximum (FWHM) of the organic light emitting diode D is narrowed.

The space-through charge transfer compound having a delayed fluorescence property has high quantum efficiency. However, since the light emitted from the space-through charge transfer compound has wide FWHM, the light from the space-through charge transfer compound has poor color purity. On the other hand, the fluorescence material has narrow FWHM and high color purity. However, since the energy level of triplet state of the fluorescence material is not engaged in the emission, the fluorescence material has low quantum efficiency.

Since the EML 340 of the organic light emitting diode D in the present disclosure includes the first layer 342, which includes space-through charge transfer compound as the dopant, and the second layer 344, which includes the fluorescence material as the dopant, the organic light emitting diode D has advantages in both the emitting efficiency and the color purity.

The energy level of triplet state of the space-through charge transfer compound is converted into the energy level of singlet state of the space-through charge transfer compound by the reverse intersystem crossing (RISC) effect, and the energy level of singlet state of the space-through charge transfer compound is transferred into the energy level of singlet state of the fluorescence material. Namely, the difference between the energy level of triplet state of the space-through charge transfer compound and the energy level of singlet state of the space-through charge transfer compound is less than 0.3 eV such that the energy level of triplet state of the space-through charge transfer compound is converted into the energy level of singlet state of the space-through charge transfer compound by the RISC effect.

As a result, the space-through charge transfer compound has an energy transfer function, and the first layer 342 including the space-through charge transfer compound is not engaged in the emission. The emission is generated in the second layer 344 including the fluorescence material.

The energy level of triplet state of the space-through charge transfer compound is converted into the energy level of singlet state of the space-through charge transfer compound by the RISC effect. In addition, since the energy level of singlet state of the space-through charge transfer compound is higher than that of the fluorescence material, the energy level of singlet state of the space-through charge transfer compound is transferred into the energy level of singlet state of the fluorescence material. As a result, the fluorescence material emits the light using the energy level of singlet state and the energy level of triplet state such that the quantum efficiency (emitting efficiency) of the organic light emitting diode D is improved.

In other words, the organic light emitting diode D and the OLED device 100 (of FIG. 7) including the organic light emitting diode D has advantages in both the emitting efficiency and the color purity.

The first and second layers 342 and 344 may further includes first and second hosts, respectively. The first and second hosts may have a percentage by weight being larger than the space-through charge transfer compound and the fluorescence material, respectively. In addition, the percentage by weight of the space-through charge transfer compound in the first layer 342 may be greater than that of the fluorescence material in the second layer 344. As a result, the energy transfer from the space-through charge transfer compound into the fluorescence material is sufficiently generated.

The energy level of singlet state of the first host is greater than that of the space-through charge transfer compound (first dopant), and the energy level of triplet state of the first host is greater than that of the space-through charge transfer compound. In addition, the energy level of singlet state of the second host is greater than that of the fluorescence material (second dopant).

When not satisfying this condition, a quenching happens at the first and second dopants or an energy transfer from the host to the dopant does not happen, and thus the quantum efficiency of the organic light emitting diode D is reduced.

For example, the second host, which is included in the second layer 344 with the fluorescence material, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the fluorescence dopant and the second layer 344 includes the space-through charge transfer compound, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Figure 10:
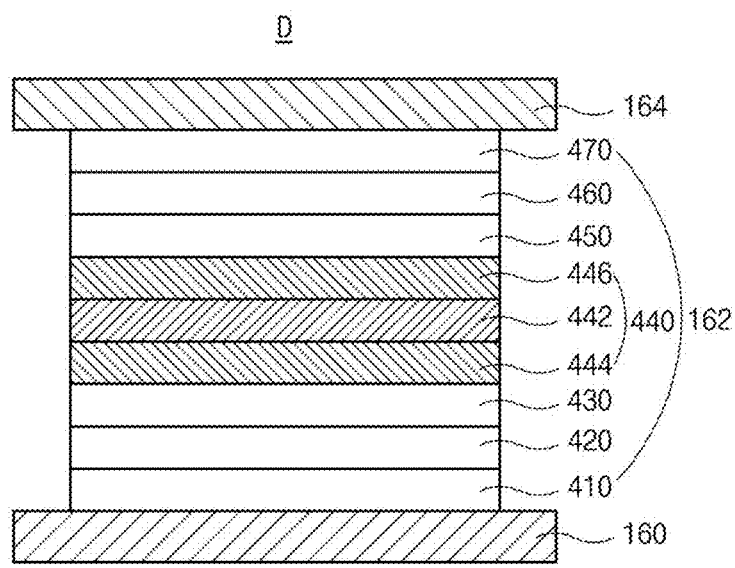
FIG. 10 is a schematic cross-sectional view of an OLED according to the present disclosure.

FIG. 10 is a schematic cross-sectional view of an organic light emitting diode (OLED) according to the present disclosure.

As shown in FIG. 10, an organic light emitting diode D includes the first and second electrodes 160 and 164, which face each other, and the organic emitting layer 162 therebetween. The organic emitting layer 162 includes an EML 440, which includes first to third layers 442, 444 and 446 and is positioned between the first and second electrodes 160 and 164, a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) may include the space-through charge transfer compound of the present disclosure as a dopant, and each of the second layer 444 (e.g., a second emitting material layer) and the third layer 446 (e.g., a third emitting material layer) may include the fluorescence material as a dopant. The fluorescence material in the second and third layers 444 and 446 may be same or different. The space-through charge transfer compound has an energy level of singlet state being larger than the fluorescence material.

In the organic light emitting diode D, the energy level of singlet state and the energy level of triplet state of the space-through charge transfer compound in the first layer 442 are transferred into the fluorescence material in the second layer 444 and/or the third layer 446 such that the emission is generated from the fluorescence material. As a result, the quantum efficiency of the OLED D is increased, and the FWHM of the OLED is narrowed.

The first to third layers 442, 444 and 446 may further include first to third hosts, respectively. The first to third hosts are same material or different materials. For example, each of the first to third hosts may be selected from materials of Formula 10.

In each of the first to third layers 442, 444 and 446, the first to third hosts may have a percentage by weight being larger than the space-through charge transfer compound and the fluorescence material, respectively. In addition, the percentage by weight of the space-through charge transfer compound (i.e., the first dopant) in the first layer 442 may be greater than that of each of the fluorescence material (i.e., the second dopant) in the second layer 444 and the fluorescence material (i.e., the third dopant) in the third layer 446.

The energy level of singlet state of the first host is greater than that of the space-through charge transfer compound, and the energy level of triplet state of the first host is greater than that of the space-through charge transfer compound. In addition, the energy level of singlet state of the second host is greater than that of the fluorescence material in the second layer 444, and the energy level of singlet state of the third host is greater than that of the fluorescence material in the third layer 446.

For example, the second host in the second layer 444 may be same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting layer and an electron blocking layer.

The third host in the third layer 446 may be same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting layer and a hole blocking layer.

The second host in the second layer 444 may be same as a material of the EBL 430, and the third host in the third layer 446 may be same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting layer and an electron blocking layer and the third layer 446 serves as an emitting layer and a hole blocking layer.

It will be apparent to those skilled in the art that various modifications and variations can be made in the embodiment of the disclosure without departing from the spirit or scope of the disclosure. Thus, it is intended that the embodiment of the disclosure cover the modifications and variations of this disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A space-through charge transfer compound of Formula (1):

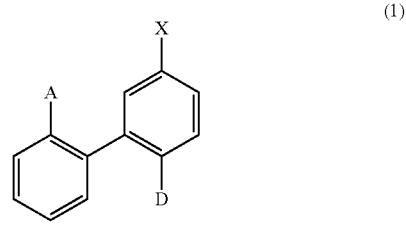

wherein:
X is H, CN, or F;
A is:

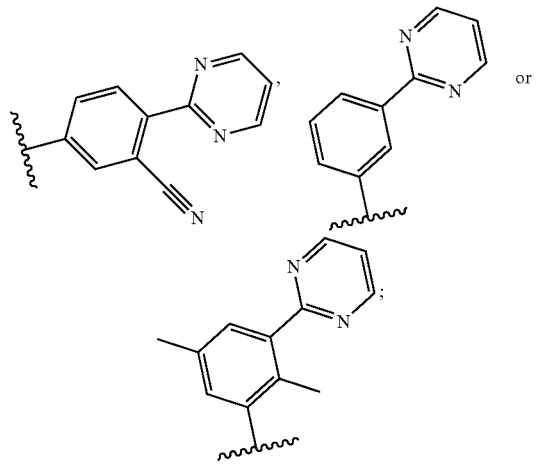

D is:

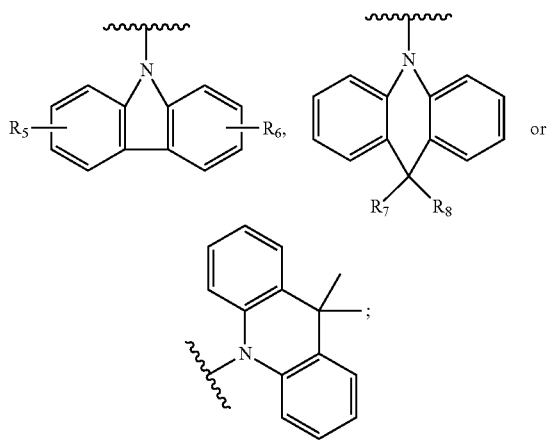

each of R7 and R8 is hydrogen, or R7 and R8 are bonded together to form a fused ring; and
each of R5 and R6 is independently selected from the group consisting of hydrogen and heteroaryl group.

2. The space-through charge transfer compound according to claim 1, wherein D is:
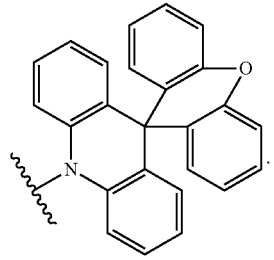 [SMILES: *N1c2ccccc2C2(c3ccccc3Oc3ccccc32)c2ccccc21]
3. The space-through charge transfer compound according to claim 1, wherein the space-through charge transfer compound is selected from the group consisting of:
compound 7
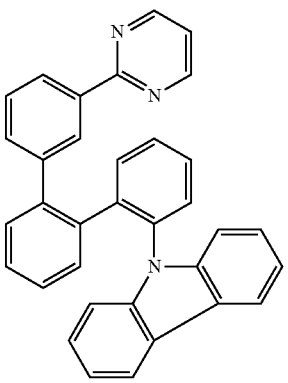
compound 8
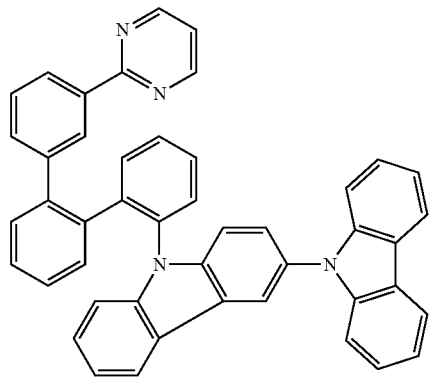
compound 9
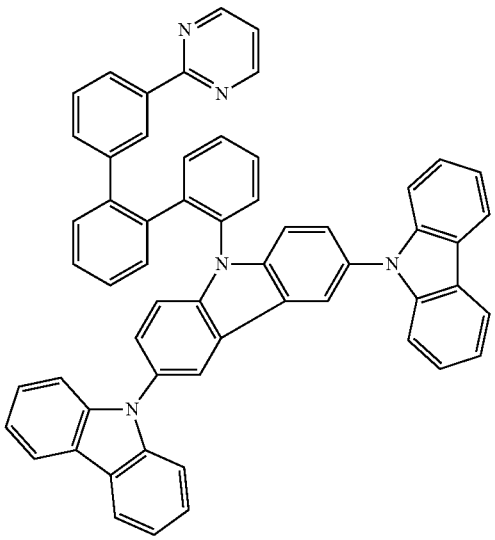
compound 10
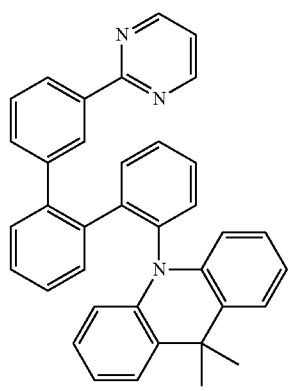
compound 11
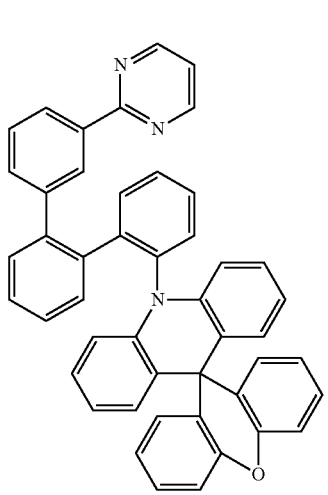

-continued

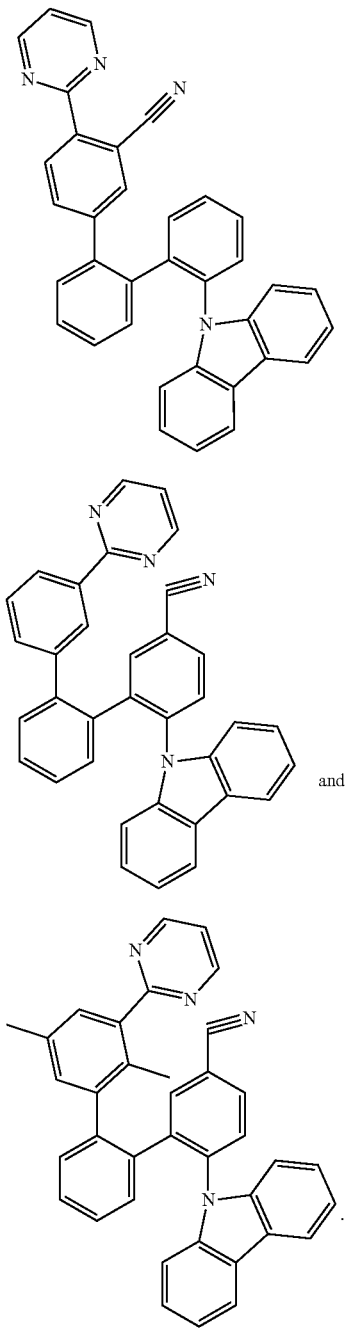

compound 12 compound 14 and compound 15

4. The space-through charge transfer compound according to claim 1, wherein a difference between an energy level of singlet state of the space-through charge transfer compound and an energy level of triplet state of the space-through charge transfer compound is less than about 0.3 eV.

5. An organic light emitting diode, comprising:
a first electrode;
a second electrode facing the first electrode; and
a first emitting material layer between the first and second electrodes, the first emitting material layer including a first host and an emitting dopant, wherein the emitting dopant includes the space-through charge transfer compound of claim 1, and wherein the first host has one of the following structures:

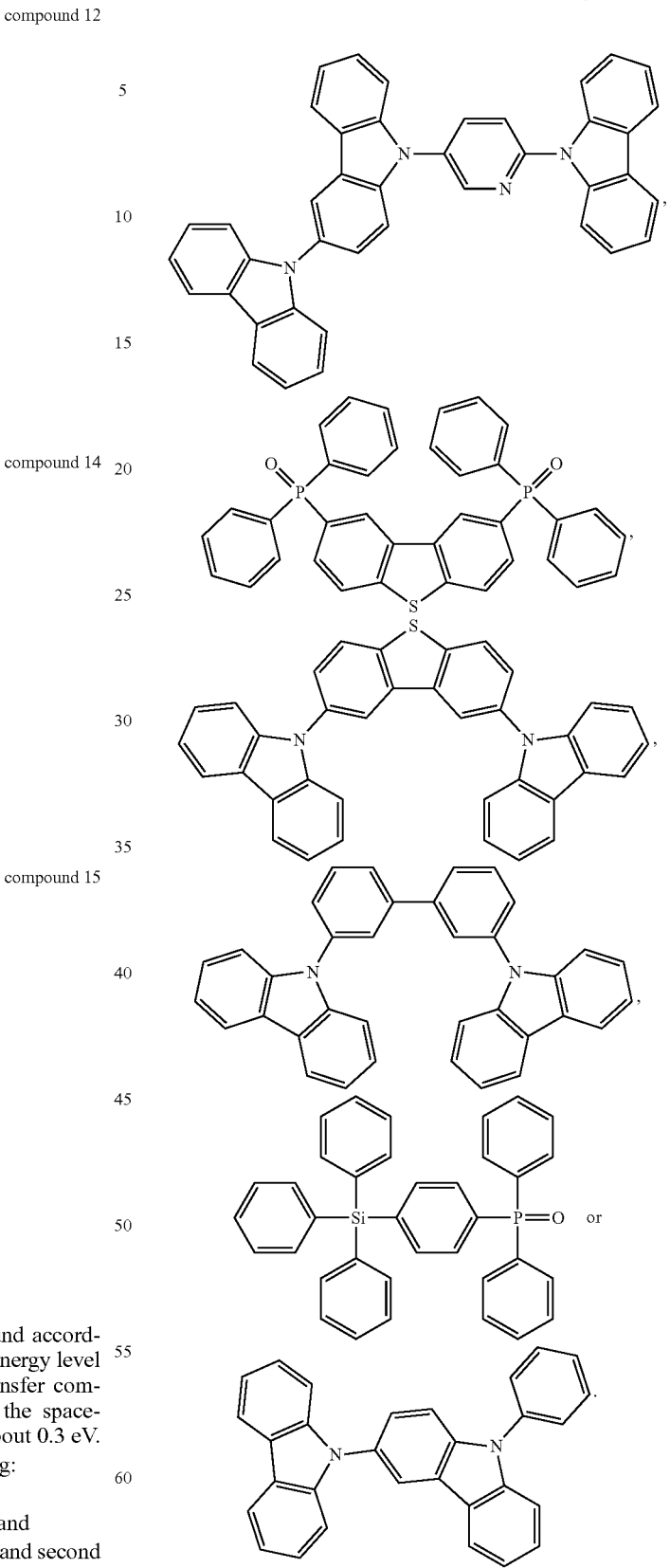

6. The organic light emitting diode according to claim 5, wherein a difference between an energy level of a highest occupied molecular orbital (HOMO) of the first host and an energy level of a HOMO of the space-through charge transfer compound or a difference between an energy level of a lowest unoccupied molecular orbital (LUMO) of the first host and an energy level of a LUMO of the space-through charge transfer compound is less than about 0.5 eV.

7. The organic light emitting diode according to claim 5, wherein:
   the first emitting material layer further includes a first dopant; and
   an energy level of singlet state of the space-through charge transfer compound is greater than an energy level of singlet state of the first dopant.

8. The organic light emitting diode according to claim 7, wherein an energy level of triplet state of the space-through charge transfer compound is smaller than an energy level of triplet state of the first host and greater than an energy level of triplet state of the first dopant.

9. The organic light emitting diode according to claim 5, further comprising:
   a second emitting material layer including a second host and a first fluorescence dopant, wherein the second emitting material layer is positioned between the first electrode and the first emitting material layer.

10. The organic light emitting diode according to claim 9, further comprising: an electron blocking layer between the first electrode and the second emitting material layer, wherein a material of the second host is the same as a material of the electron blocking layer.

11. The organic light emitting diode according to claim 9, further comprising: a third emitting material layer including a third host and a second fluorescent dopant, wherein the third emitting material layer is positioned between the second electrode and the first emitting material layer.

12. The organic light emitting diode according to claim 11, further comprising: a hole blocking layer between the second electrode and the third emitting material layer, wherein a material of the third host is the same as a material of the hole blocking layer.

13. The organic light emitting diode according to claim 11, wherein an energy level of singlet state of the space-through charge transfer compound is greater than each of an energy level of singlet state of the first fluorescent dopant and an energy level of singlet state of the second fluorescent dopant.

14. The organic light emitting diode according to claim 11, wherein:
   an energy level of singlet state and an energy level of triplet state of the first host is greater than an energy level of singlet state and an energy level of triplet state of the space-through charge transfer compound, respectively; and
   an energy level of singlet state of the second host is greater than an energy level of singlet state of the first fluorescent dopant, and an energy level of singlet state of the third host is greater than an energy level of singlet state of the second fluorescent dopant.

15. The organic light emitting diode according to claim 9, wherein an energy level of singlet state of the space-through charge transfer compound is greater than an energy level of singlet state of the first fluorescent dopant.

16. The organic light emitting diode according to claim 9, wherein:
   an energy level of singlet state and an energy level of triplet state of the first host are greater than an energy level of singlet state and an energy level of triplet state of the space-through charge transfer compound, respectively; and
   an energy level of singlet state of the second host is greater than an energy level of singlet state of the first fluorescent dopant.

17. The organic light emitting diode according to claim 5, wherein the space-through charge transfer compound is one of the following compounds:

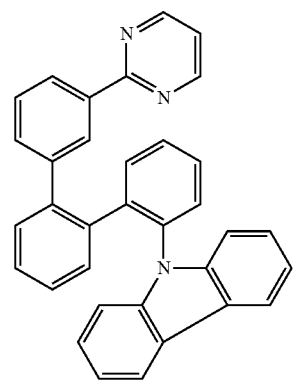

compound 7

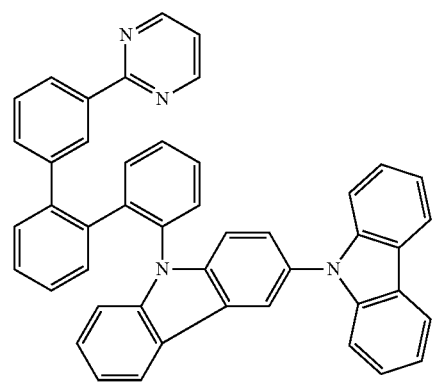

compound 8

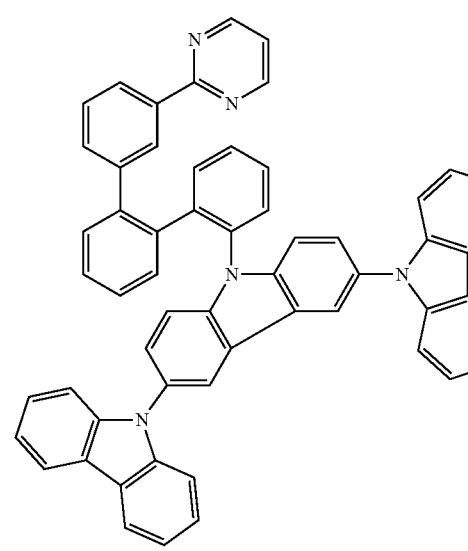

compound 9

-continued compound 10

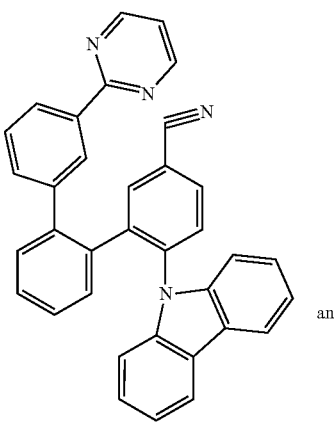

compound 11

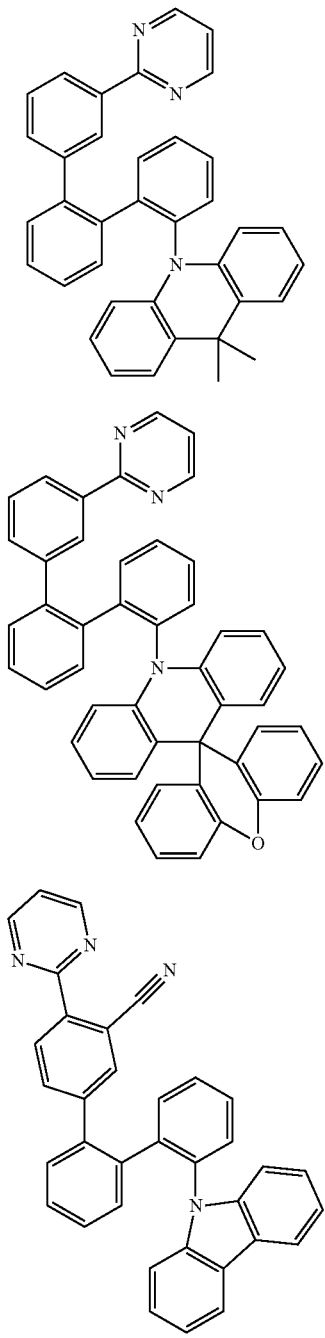

compound 12

-continued compound 14

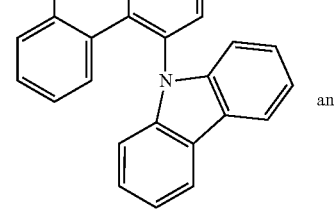

and compound 15

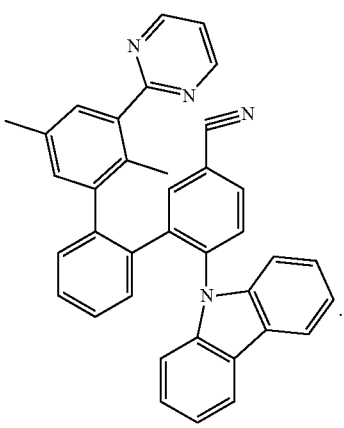

18. An organic light emitting display device, comprising:
    a substrate;
    the organic light emitting diode of claim 5 disposed on the substrate; and
    an encapsulation film covering the organic light emitting diode.

19. The space-through charge transfer compound according to claim 1, wherein X is CN or F.

20. The organic light emitting diode according to claim 5, wherein an amount of the emitting dopant is 1% to 30% by weight with respect to the first host.

21. The organic light emitting diode according to claim 5, wherein the first emitting material layer provides blue light.

* * * * *